United States Patent
Young

(10) Patent No.: US 11,759,589 B2
(45) Date of Patent: Sep. 19, 2023

(54) POWERING BREATHING APPARATUS

(71) Applicant: Fisher & Paykel Healthcare Limited, Auckland (NZ)

(72) Inventor: Alex Young, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 675 days.

(21) Appl. No.: 16/617,388

(22) PCT Filed: May 25, 2018

(86) PCT No.: PCT/IB2018/053724
§ 371 (c)(1),
(2) Date: Nov. 26, 2019

(87) PCT Pub. No.: WO2018/215978
PCT Pub. Date: Nov. 29, 2018

(65) Prior Publication Data
US 2021/0008312 A1    Jan. 14, 2021

Related U.S. Application Data

(60) Provisional application No. 62/511,820, filed on May 26, 2017.

(51) Int. Cl.
*A61M 16/00*    (2006.01)
*G06F 21/62*    (2013.01)

(52) U.S. Cl.
CPC ....... *A61M 16/024* (2017.08); *G06F 21/6245* (2013.01); *A61M 2205/15* (2013.01);
(Continued)

(58) Field of Classification Search
CPC .......... A61M 16/00; A61M 2205/8257; A61M 2205/8237; A61M 2205/82–8212; A61M 2205/8262; G06F 1/1635
See application file for complete search history.

(56) References Cited

U.S. PATENT DOCUMENTS

| | | | |
|---|---|---|---|
| 4,587,967 A * | 5/1986 | Chu ...................... | A61M 16/12 128/204.21 |
| 7,252,088 B1 | 8/2007 | Nieves-Ramirez | |

(Continued)

FOREIGN PATENT DOCUMENTS

| | | |
|---|---|---|
| CN | 105833401 | 8/2016 |
| CN | 106668998 | 5/2017 |

(Continued)

OTHER PUBLICATIONS

International Search Report for International App. No. PCT/IB2018/053724, dated Aug. 28, 2018, in 3 pages.

(Continued)

*Primary Examiner* — Kendra D Carter
*Assistant Examiner* — Thomas W Greig
(74) *Attorney, Agent, or Firm* — Knobbe, Martens, Olson & Bear, LLP

(57) ABSTRACT

Described herein is a respiratory therapy system comprising: a primary power supply, a secondary power supply, and a breathing apparatus configured to provide respiratory therapy. The breathing apparatus comprises a controller. There is a connection between the primary power supply and the breathing apparatus configured to facilitate transmission of power and data between the primary power supply and the breathing apparatus. The controller is configured to monitor a parameter of the primary power supply, and disengage the primary power supply if the parameter differs from a parameter threshold. The controller is configured to engage the secondary power supply on disconnection of the primary power supply such that the breathing apparatus can continue operation without interruption.

19 Claims, 20 Drawing Sheets

(52) U.S. Cl.
CPC .............. *A61M 2205/3331* (2013.01); *A61M 2205/3368* (2013.01); *A61M 2205/3576* (2013.01); *A61M 2205/8206* (2013.01); *A61M 2205/8237* (2013.01)

(56) References Cited

U.S. PATENT DOCUMENTS

| | | | |
|---|---|---|---|
| 7,721,736 B2 * | 5/2010 | Urias | A61M 16/0063 128/204.26 |
| 8,042,535 B2 | 10/2011 | Kenyon et al. | |
| 8,302,600 B2 * | 11/2012 | Andrieux | H01M 10/425 128/204.21 |
| 9,233,219 B2 | 1/2016 | Young et al. | |
| 9,852,098 B2 * | 12/2017 | Gagne-Keats | H04M 1/72409 |
| 10,381,849 B2 | 8/2019 | Wing et al. | |
| 10,960,158 B2 | 3/2021 | Mahadevan et al. | |
| 2004/0119341 A1 * | 6/2004 | Hickle | A61M 16/01 307/66 |
| 2006/0181153 A1 * | 8/2006 | Oberle | H02J 9/062 307/112 |
| 2008/0000474 A1 | 1/2008 | Jochle | |
| 2008/0011296 A1 | 1/2008 | Schatzl | |
| 2008/0264417 A1 | 10/2008 | Manageł et al. | |
| 2010/0065054 A1 * | 3/2010 | Bowman | A61M 16/0051 128/204.21 |
| 2011/0126829 A1 | 6/2011 | Carter et al. | |
| 2011/0197882 A1 * | 8/2011 | Truschel | A61M 16/0057 429/99 |
| 2013/0333697 A1 * | 12/2013 | Carter | H01M 10/482 429/61 |
| 2016/0193437 A1 | 7/2016 | Bao et al. | |
| 2017/0293335 A1 * | 10/2017 | Dunstan | H02J 50/10 |

FOREIGN PATENT DOCUMENTS

| | | |
|---|---|---|
| WO | WO 2010/027282 | 3/2010 |
| WO | WO 2015/084255 | 6/2015 |

OTHER PUBLICATIONS

International Preliminary Report on Patentability in corresponding International Patent Application No. PCT/IB2018/053724, dated Nov. 26, 2019, in 6 pages.

* cited by examiner

Table 1

| Profile | 5v | 12v | 20v |
|---|---|---|---|
| 0 | Reserved | | |
| 1 | 2A, 10W | | |
| 2 | 2A, 10W ⟷ 1.5A, 18W | | |
| 3 | 2A, 10W ⟷ 3A, 36W | | |
| 4 | 2A, 10W ⟷ 3A, 36W ⟷ 3A, 60W | | |
| 5 | 2A, 10W ⟷ 5A, 60W ⟷ 5A, 100W | | |

*FIGURE 5*

POWERING BREATHING APPARATUS

FIELD OF THE INVENTION

The present disclosure relates to a method and apparatus for powering a breathing apparatus using a USB connection and power specification.

BACKGROUND OF THE INVENTION

Continuous positive airway pressure (CPAP) apparatus are used to treat obstructive sleep apnoea. CPAP apparatus need a suitable power supply to power the electronics/controller, blower and/or humidifier. Traditional CPAP apparatus cannot be powered via a USB connection as sufficient power cannot be delivered by the USB connection. The present inventors have overcome this problem, which will be disclosed in this specification. This enables an alternative option for powering a CPAP apparatus, which can lead to usability improvements such as portability. The disclosed solution may also be applied to suitably power any other breathing apparatus with similar shortcomings as those identified in traditional CPAP apparatus.

SUMMARY OF INVENTION

It is an object of the present invention to provide a breathing apparatus, and optionally an associated method, that can be powered by USB connection and/or a USB power specification.

In one aspect, the invention comprises a respiratory therapy system comprising: a primary power supply, a secondary power supply, a breathing apparatus configured to provide respiratory therapy comprising a controller, a connection between the primary power supply and the breathing apparatus configured to facilitate transmission of power and data between the primary power supply and the breathing apparatus, wherein the controller is configured to monitor a parameter of the primary power supply, and disengage the primary power supply if the parameter differs from a parameter threshold, and wherein the controller is configured to engage the secondary power supply on disconnection of the primary power supply such that the breathing apparatus can continue operation without interruption.

Optionally, the breathing apparatus comprises a power module for controlling power distribution.

Optionally, the controller is configured to monitor the parameter of the primary power supply, and disengage the power module from the primary power supply if the parameter differs from the parameter threshold.

Optionally, the controller is configured to engage the power module with the secondary power supply on disconnection of the primary power supply such that the uninterrupted supply of power is provided to the breathing apparatus.

Optionally, the power module is disengaged from the primary power supply if the parameter exceeds the parameter threshold.

Optionally, the power module is disengaged from the power supply if the parameter is less than the parameter threshold.

Optionally, the power module is disengaged from the power supply if the parameter is equal to the parameter threshold.

Optionally, the controller configures the power module to provide power from the secondary power supply to the primary power supply following engagement of the secondary power supply.

Optionally, the breathing apparatus includes a data module configured to transmit to and receive data from the primary power supply via the connection.

Optionally, the primary power supply includes a sensor.

Optionally, the primary power supply is configured to transmit sensor data from the sensor to the data module.

Optionally, the sensor is powered by the primary power supply.

Optionally, the sensor is powered by the secondary power supply after engagement of the power module with the secondary power supply via the connection.

Optionally, the sensor is a temperature sensor and the sensor data is temperature data indicative of a temperature of the primary power supply.

Optionally, the parameter threshold is indicative of a temperature threshold.

Optionally, the temperature threshold is indicative of an over temperature condition of the primary power supply.

Optionally, the sensor is a voltage sensor and the sensor data is voltage data indicative of an input voltage of the primary power supply.

Optionally, the parameter threshold is indicative of an input voltage threshold.

Optionally, the input voltage threshold is indicative of an overvoltage threshold of the primary power supply.

Optionally, the input voltage threshold is indicative of an undervoltage threshold of the primary power supply.

Optionally, the sensor data is power data indicative of the supply of power from the primary power supply to the breathing apparatus.

Optionally, the sensor data is voltage data indicative of an input voltage from the primary power supply.

Optionally, the parameter threshold is indicative of an input voltage threshold.

Optionally, the input voltage threshold is indicative of an overvoltage condition.

Optionally, the input voltage threshold is indicative of an undervoltage condition.

Optionally, the connection is further configured to facilitate transmission of power and data between the breathing apparatus and a peripheral computing device.

Optionally, the data is device data communicated from the device to the peripheral device.

Optionally, the device data comprises usage data.

Optionally, the device data comprises pressure, flow, temperature, humidity, compliance, duration, altitude, leak, equipment identification, software, diagnostic and/or user feedback data.

Optionally, the device data is encrypted.

Optionally, the data is peripheral device data communicated from the peripheral computing device to the breathing apparatus.

Optionally, the peripheral device data comprises update data.

Optionally, the update data comprises updated respiratory therapy settings.

Optionally, the update data comprises updated operating software and/or firmware.

Optionally, the peripheral device data comprises a patient profile.

Optionally, after a period of time, the controller is configured to disengage the power module from the internal power supply, and engage the power module with the power supply.

Optionally, the period of time is a predetermined period of time.

Optionally, the controller is configured to detect a magnitude of a difference between the parameter threshold and the monitored parameter.

Optionally, the period of time is a function of the difference.

Optionally, the breathing apparatus includes a circuit that includes the controller, power module and data module.

Optionally, the controller is an electromechanical controller or a processor.

Optionally, the secondary power supply is an internal battery.

Optionally, the respiratory therapy system is configured such that the primary power supply charges the internal battery when the battery is not charged to full capacity and the primary power supply is engaged.

Optionally, the connection comprises an electrical cord.

Optionally, the connection comprises a breathing apparatus port on the breathing apparatus configured to receive the electrical cord.

Optionally, the electrical cord is removable from the breathing apparatus port.

Optionally, the breathing apparatus port is a USB-C port.

Optionally, the electrical cord is a USB-C cable.

Optionally, an uninterrupted supply of power is provided to the breathing apparatus.

Optionally, the connection facilitates simultaneous bi-directional power and data transfer.

Described herein is a respiratory therapy system comprising: a primary power supply, a breathing apparatus configured to provide respiratory therapy comprising: a controller, a connection between the primary power supply and the breathing apparatus configured to facilitate transmission of power and data between the primary power supply and the breathing apparatus, wherein the controller is configured to monitor a parameter of the primary power supply, and engage a secondary power supply if the parameter differs from a parameter threshold, and wherein the controller is configured to disengage the primary power supply upon engagement of the secondary power supply such that the breathing apparatus continues operation without interruption.

Optionally, the primary power supply includes a USB-C port, and the connection between the primary power supply and the breathing apparatus is a USB-C connection via the USB-C cable.

Optionally, the peripheral computing device includes a USB-C port, and the connection between the breathing apparatus and the peripheral computing device is a USB-C connection via the USB-C cable.

Also described herein is a method of controlling a breathing apparatus comprising: monitoring a parameter of a primary power supply via a connection between the primary power supply and the breathing apparatus configured to facilitate transmission of power and data between the primary power supply and the breathing apparatus, determining that the parameter differs from a parameter threshold, disengaging a power module of the breathing apparatus from the primary power supply, and engaging the power module with a secondary power supply on disconnection of the primary power supply such that the breathing apparatus can continue operation without interruption.

Optionally, an uninterrupted supply of power is provided to the breathing apparatus.

Also described herein is a breathing apparatus adapted to be powered via a USB connection, wherein the breathing apparatus is configured such that the power requirements of the breathing apparatus in use can be delivered by a USB connection.

Optionally, the breathing apparatus is configured by one or more of:
CPAP miniaturization
no humidification
reduced humidification
passive humidification
improved humidification efficiency
improved motor efficiency
improved blower efficiency.

Optionally, the USB connection is a USB-C connection.

Optionally, the USB-C connection delivers power according to a USB-PD standard.

Optionally, the requirements of the breathing apparatus are one or more of:
a power rating less than or equal to 100 W
a power rating less than or equal to 60 W
A power rating less than or equal to 36 W.

Optionally, the USB connection can deliver one or more of:
a power rating of 10 W or less
a power rating of 18 W or less
a power rating of 36 W or less
a power rating of 60 W or less
a power rating of 100 W or less.

Optionally, the USB connection is one of the following:
tethered
non-tethered
wireless.

Optionally, the USB connection is tethered and comprises one of the following:
a power adapter comprising a plug, and a lead comprising a USB connector, wherein the lead is attached to the power adapter
a power adapter adapted to receive power from a car power adapter, and a lead comprising a USB connector, wherein the lead is attached to the power adapter
a battery pack and at least one lead, wherein each lead comprises a USB connector
a USB cable tethered to the breathing apparatus.

Optionally, the USB connection is non-tethered and comprises one of the following:
a power adapter module comprising a plug and a socket, and a lead module comprising a USB connector at both ends
a battery pack module comprising at least one socket, and at least one lead module comprising a USB connector at both ends of the lead module
a universal power adapter module comprising a power socket adapted to mate with a power plug of a domestic power adapter, the domestic power adapter comprising a first lead socket, the universal power adapter module optionally comprising a second lead socket;
a lead comprising a USB connector at both ends;
wherein, the lead is adapted to mate with either the first lead socket and/or the second lead socket.

Optionally, the breathing apparatus is:
CPAP
NIV PAP
Bi-level PAP
Flow generator
or other nasal or oral high flow therapy.

Optionally, the breathing apparatus is one or more of:
minituarised
portable wearable modular reduced/small form factor/footprint.

Also described herein is a system comprising a power supply, a USB connection, and a breathing apparatus, wherein either the USB connection, or the breathing apparatus, or both are adapted such that the power requirements of the breathing apparatus can be delivered by the USB connection.

A USB connection refers to a USB cable or similar comprising a conductor and USB standard connectors that can be plugged into a power source or other power supply and an apparatus to be powered to transfer power across the USB connection to the apparatus to be powered. The USB power specification defines how the USB connection transfers power. The USB connection preferably is a USB-C standard connection with USB-C connectors, and the USB power specification is preferably the USB-PD power specification. However, alternatives are possible.

The inventors have determined a combination of breathing apparatus configuration and USB connection/power specification that allows for powering the breathing apparatus, where that power requirement of the breathing apparatus does not exceed what can be delivered by the USB connection and/or USB power specification.

The breathing apparatus is configured such that its power requirements do not exceed those of the USB connection and/or USB power specification for delivery of power on that USB connection. This can be achieved, for example, by one or more of reducing humidity power requirements, or removing humidity functionality, using passive humidity techniques, improving the humidifier efficiency, improving motor efficiency and/or improving blower efficiency.

In this specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth. The invention consists in the foregoing and also envisages constructions of which the following gives examples only.

As used herein the term '(s)' following a noun means the plural and/or singular form of that noun.

As used herein the term 'and/or' means 'and' or 'or', or where the context allows both. The invention consists in the foregoing and also envisages constructions of which the following gives examples only.

BRIEF DESCRIPTION OF DRAWINGS

FIG. 5 shows the power configurations available across power profiles 0-5, within the USB-PD power specification.

OVERVIEW OF THE DETAILED DESCRIPTION

Figure 1A:
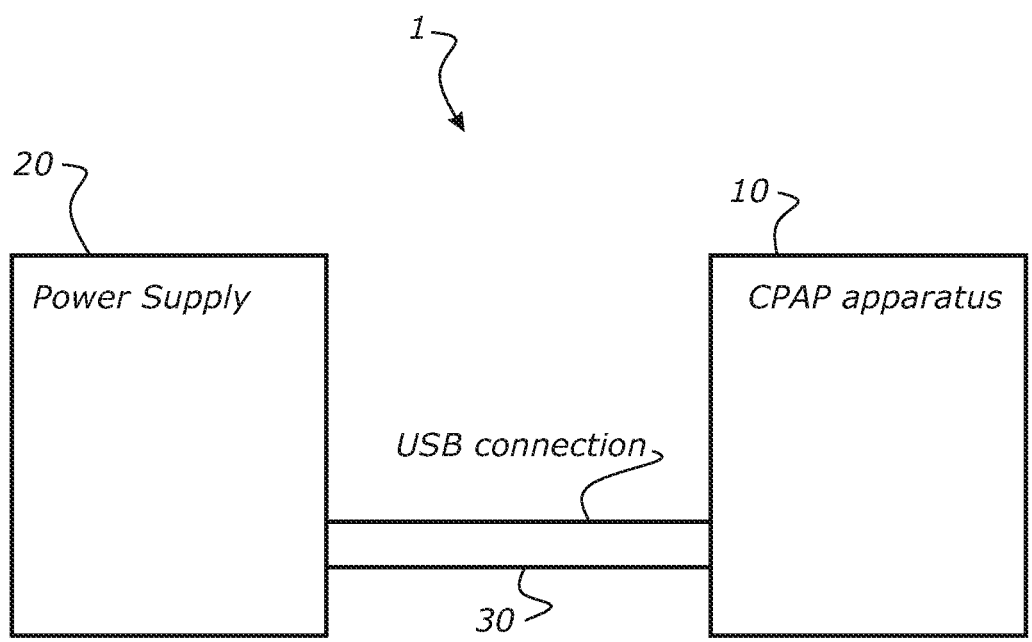
FIG. 1a shows a block diagram of a CPAP apparatus receiving power from a USB connection.

FIG. 1a shows a block diagram of a respiratory therapy system 1 by way of example. The respiratory therapy system 1 comprises a continuous positive airway pressure (CPAP) apparatus 10 powered from a power supply 20 using a USB connection 30, which operates in accordance with a prescribed USB power specification. In at least one configuration, the respiratory therapy system 1, instead of a CPAP apparatus may comprise another respiratory therapy device, such as a nasal high flow therapy device or a bi-level positive airway pressure device. The USB connection 30 enables coupling between the power supply 20 and the CPAP apparatus 10 via USB standard, or USB technical specification. The USB connection 30 comprises cable, connectors and/or other hardware capable of effecting the coupling between the power supply 20 and the CPAP apparatus 10, or a combination thereof in accordance with USB standard/s and/or USB technical specification/s. The power supply 20 could be any suitable supply, such as a mains supply, battery, UPS, or the like. The CPAP apparatus 10 is configured and the USB connection 30 specifications are chosen such that the power requirements of the CPAP apparatus 10 do not exceed those that can be delivered by the USB connection 30, i.e. the CPAP apparatus 10 can be powered from the power supply 20 via the USB connection 30. It is assumed that the power supply 20 can supply sufficient power. Traditional CPAP apparatus 10 cannot be powered via a USB connection 30 as sufficient power cannot be delivered by the USB connection 30. The present inventors have overcome this problem. This enables an alternative option for powering a CPAP apparatus 10, which can lead to usability improvements such as portability. The disclosed solution may also be applied to suitably power any other breathing apparatus with similar shortcomings as those identified in traditional CPAP apparatus 10. Such breathing apparatus may include, but is not limited to: NIV PAP apparatus, Bi-level PAP apparatus, high flow therapy apparatus, etc.

The remainder of the detailed description will be structured as follows. Section 1 describes an exemplary embodiment of a respiratory therapy system that explains how a CPAP apparatus can be powered using a USB connection. Section 2 describes a dual power supply embodiment, which demonstrates one application of providing a USB connection to a breathing apparatus. Section 3 describes a peripheral computing device embodiment, which demonstrates another application of providing a USB connection to a breathing apparatus.

1. Overview of the First Embodiment

Figure 1B:
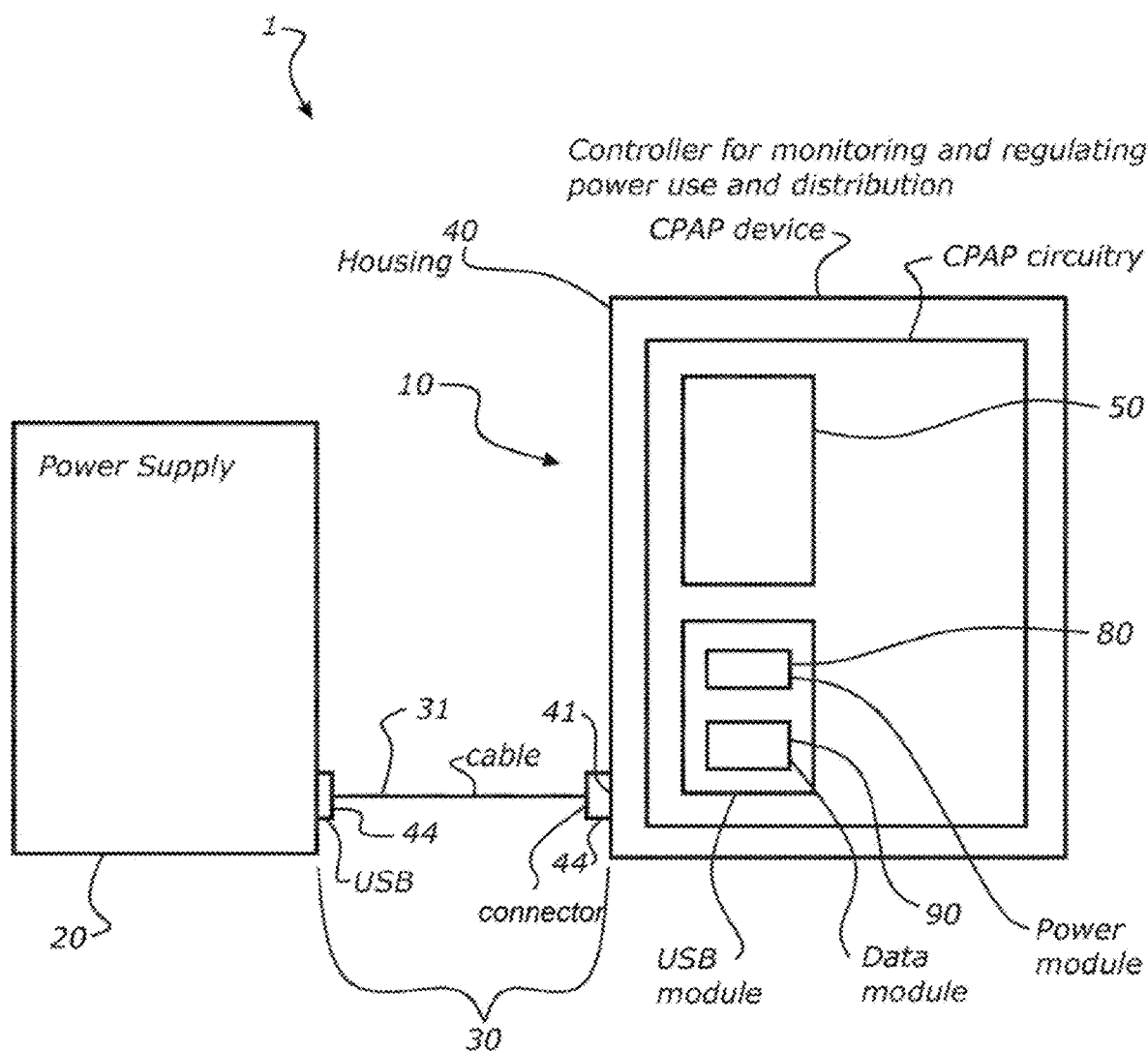
FIG. 1b shows a block diagram of a CPAP apparatus receiving power from a USB-C cable.

One embodiment of a respiratory therapy system comprising a CPAP apparatus 10, power supply 20 and a USB connection 30 is shown in FIG. 1b. The CPAP apparatus 10 comprises a housing 40, a controller 50 (and other control circuitry), sensors, a blower (optionally a humidifier), and any other components that are typical in a CPAP apparatus 10. It further comprises a power module 80 for powering the components of the CPAP apparatus 10. The housing 40 has a USB port 41 for receiving a USB connector 44 of a USB connection 30. The port is internally coupled to the power module 80, controller 50 and other components of the CPAP apparatus 10 so that data and/or power can be received and utilised by the CPAP apparatus 10 as required. Preferably the USB port 41 is a USB-C port for receiving the connecting portion of a USB-C connection, such as a USB-C power/data transfer cable, or other such connection that can carry and supply power. Preferably, the USB-C connection carries power according to the USB-PD standard, although other standards could be used. The USB-C connection standard can be found, for example, here (http://www.usb.org/developers/usbtypec/), and is incorporated herein by reference in its entirety. The USB-PD standard can be found, for example, here (http://www.usb.org/developers/powerdelivery/), and is incorporated herein by reference in its entirety. The CPAP apparatus 10 is configured for connecting to such a USB-C connection, which itself is connected to an external power supply 20. Once connected, the power module 80 can receive power via the USB-C connection from the external power supply 20 and transfer it as required to components to power the CPAP apparatus 10. Data transfer can also take place to and from the CPAP apparatus 10 via the data module 90.

The CPAP apparatus 10 is configured such that its power requirements do not exceed those of the USB connection 30 and/or what USB power specification can deliver, so that the CPAP apparatus 10 can be powered from the power supply 20 using the USB connection 30 which delivers power according to the USB power specification. Preferably, the USB connection 30 is a USB-C connection comprising, a conductor (e.g. cable), and USB-C connectors attached at either end of the conductor. This enables connection between the power supply 20 and the CPAP apparatus 10. In this case, the USB port 41 on the housing 40 of the CPAP apparatus 10 is adapted to mate with a USB-C connector.

Preferably, the CPAP apparatus 10 is configured so that its overall power requirements/consumption is less than about 100 W, the maximum that can be supplied by the USB-C connection and USB-PD standard. More preferably, the CPAP apparatus 10 is configured so that its overall power requirements/consumption is less than about 60 W (12V, 5 A). More preferably, the CPAP apparatus 10 is configured so that its overall power requirements/consumption is less than about 36 W (12V, 3 A—if the cable supports a current of 3 A or less then EMCA (Electronically Marked Cable Assembly) is not required). It is preferable that the CPAP apparatus 10 components are adapted to operate at an input voltage of 12V, although other voltages could be used.

A USB-C connection 30 is capable of supplying (by default) 5V at 1.5 A or 3 A. This enables a relatively high power transfer for the size of the cable. Furthermore, the technology is capable of transferring up to 100 W of power with an envelope limited to 20V and 5 A. The transfer of power at 12V can be advantageous for future CPAP development for a number of reasons. For instance, a large variety of mass produced high capacity lithium ion batteries operate at 12V. Furthermore, 12V is a standard voltage for numerous other batteries (for instance standard car batteries).

The power supply 20 represented in the block diagram can represent any source of power that can appropriately be used to power a CPAP apparatus 10.

Attention will now turn to each of main components shown in the block diagram in FIG. 1a in greater detail: 1) CPAP, 2) USB connection, and 3) power supply. Section 1.2explains power requirements and various methods of minimising power consumption in a CPAP apparatus 10. In particular this section describes the physical and electrical properties that allow a CPAP apparatus 10 to be adapted to be powered using this preferred embodiment. Section 1.3 describes a USB-C cable as a preferred embodiment of the USB connection 30. Section 1.4 describes some suggested power supply 20 examples that may be used to power a CPAP apparatus 10 using a USB connection 30, preferably a USB-C cable and connector.

1.2. CPAP Requirements and Configuration

Traditionally, CPAP apparatus 10 draws more than 100 W during operation. They are powered from a mains power supply, and cannot run from power transferred by a USB connection 30. The apparatus 10 as disclosed herein has been configured to draw less than 100 W. This will be described further now.

The following description relates to the modifications made to a CPAP apparatus 10 to enable the CPAP apparatus 10 to be powered from a power supply via a USB connection 30 that conducts power according to a USB power specification. However, the following description can also apply to any other breathing apparatus, such as NIV PAP apparatus, Bi-level PAP apparatus, high flow therapy apparatus or the like.

1.2.1 CPAP Power Specification Requirements

Embodiments disclosed comprise adapting the CPAP apparatus 10 to allow the device to operate with a lower power rating compared to what is already known in the art so that it can receive all its power requirements via a USB connection 30. This can be achieved by firstly, using a USB connection 30 with a higher power rating specified in a USB power specification, and/or secondly, reducing CPAP power requirements. This facilitates power delivery to the CPAP apparatus 10 without exceeding the power specification of the USB connection 30.

As noted earlier, preferably, the peak power consumption for a CPAP apparatus 10 is at, or less than 36 W (12V and 3 A). Configuring a CPAP 10 to take power load of 36 W is desirable, because it facilities the transfer of power at 12V, a common standard used in lithium ion batteries and other batteries. Optionally, the peak power consumption can be 60 W (12V and 5 A). This is more practical, as a higher voltage and current can be used. Peak power consumption may be up to 100 W (20V and 5 A). This is more practical, as higher voltage and current can be used. However, EMCA is required for any peak power configuration delivering a current in excess of 3 A. The CPAP apparatus 10 can be adapted to receive power with the specifications disclosed above, with either alternating current (AC) or direct current (DC). If the CPAP apparatus 10 is adapted to receive an AC power supply, the CPAP apparatus 10 will also be adapted to convert the incoming power source into DC using techniques commonly used by those skilled in the art.

1.2.2 CPAP Components and Constraints

A CPAP apparatus 10 normally comprises a blower or an air inlet adapted to receive a gas source at positive pressure. Optionally, a CPAP apparatus 10 can be adapted to include a humidification unit, including but not restricted to a humidification chamber and a heater plate. Sensors that measure temperature, humidity, flow rate or power consumption may also be included in a CPAP apparatus 10. A CPAP apparatus 10 may also include a controller 50 to control operation of the CPAP apparatus 10, including power allocation and consumption. To operate, a CPAP apparatus 10 must have a power supply that is either internal (e.g. supplied from a removable, rechargeable battery or coaxial power supply port) or external (e.g. supplied from the mains power supply), or both.

1.2.3 Reducing CPAP Power Consumption

A CPAP apparatus 10 as disclosed that can be powered via a USB connection 30 can be configured by one or more of the following to reduce power consumption.

1.2.3.1 CPAP Miniaturization

The power load of a CPAP apparatus 10 can be significantly reduced by downscaling CPAP in its entirety. One option is to redesign CPAP devices into wearable devices.

1.2.3.1 No Humidity

In another option the CPAP apparatus 10 can be designed without any humidification functionality. This can be achieved by implementing a switching mechanism capable of switching off the humidification function indefinitely and/or permanently. Alternatively the CPAP apparatus 10 can be designed without any humidifier.

1.2.3.2 Reduced Humidity

In another option, a humidifier and/or humidification functionality are provided in the CPAP apparatus 10, but modified to reduce power consumption. This can be achieved by implementing a controller adapted to monitor power consumption and/or switch off humidification temporarily when power conservation is necessary and/or desired.

1.2.3.3 Passive Humidification

In another option, passive humidification is provided by way of an HME (heat and moisture exchanger), "cold passover", wicking, or similar.

1.2.3.4 Improved Humidity Efficiency

In another option, a humidifier and humidification functionality are provided, but with modifications to improve efficiency relating to mechanical, circuitry, or control software design, or a combination thereof.

1.2.3.5 Improved Motor Efficiency

In another option, the motor in the blower of the CPAP apparatus 10 is modified to mitigate eddy current losses.

1.2.3.6 Improved Flow Path Efficiency

In another option, the blower of the CPAP apparatus 10 is modified to reduce air drag. One example, albeit not limited to this example, is to implement a recirculation passage in the blower so as to stabilise the flow of air throughout the blower, as well as stabilise the air flow from the blower output. Another example, albeit not limited to this example, is to reduce dead space in the flow path to remove the need for flow biasing to flush carbon dioxide out of the flow path.

1.2.3.7 General Modification Considerations

In addition to the options above, a CPAP apparatus 10 could be modified in any manner that reduces power requirements to a level that is deliverable from a USB connection 30. Some general design considerations are set out for such modifications.

Figure 4A:
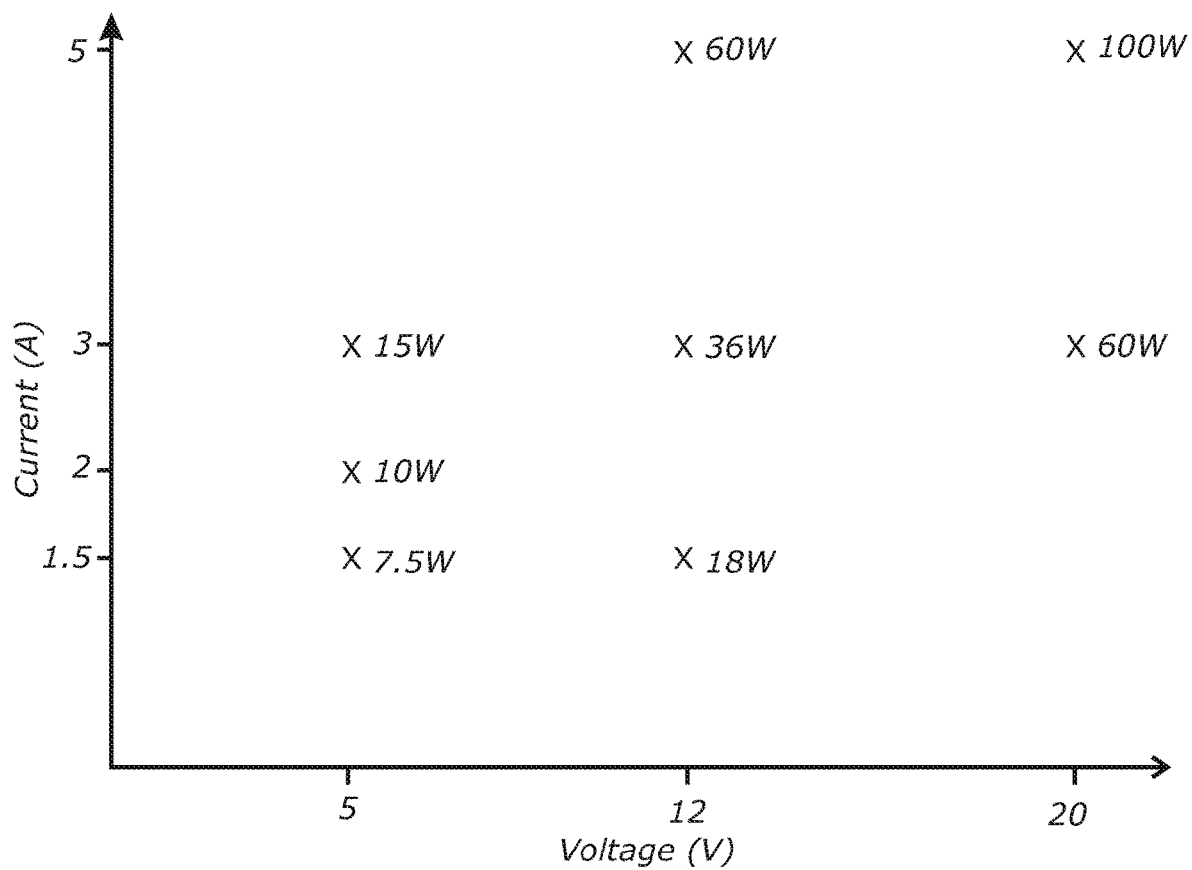
FIG. 4a shows the power configurations available with USB-C and USB-PD power specifications.
Figure 4B:
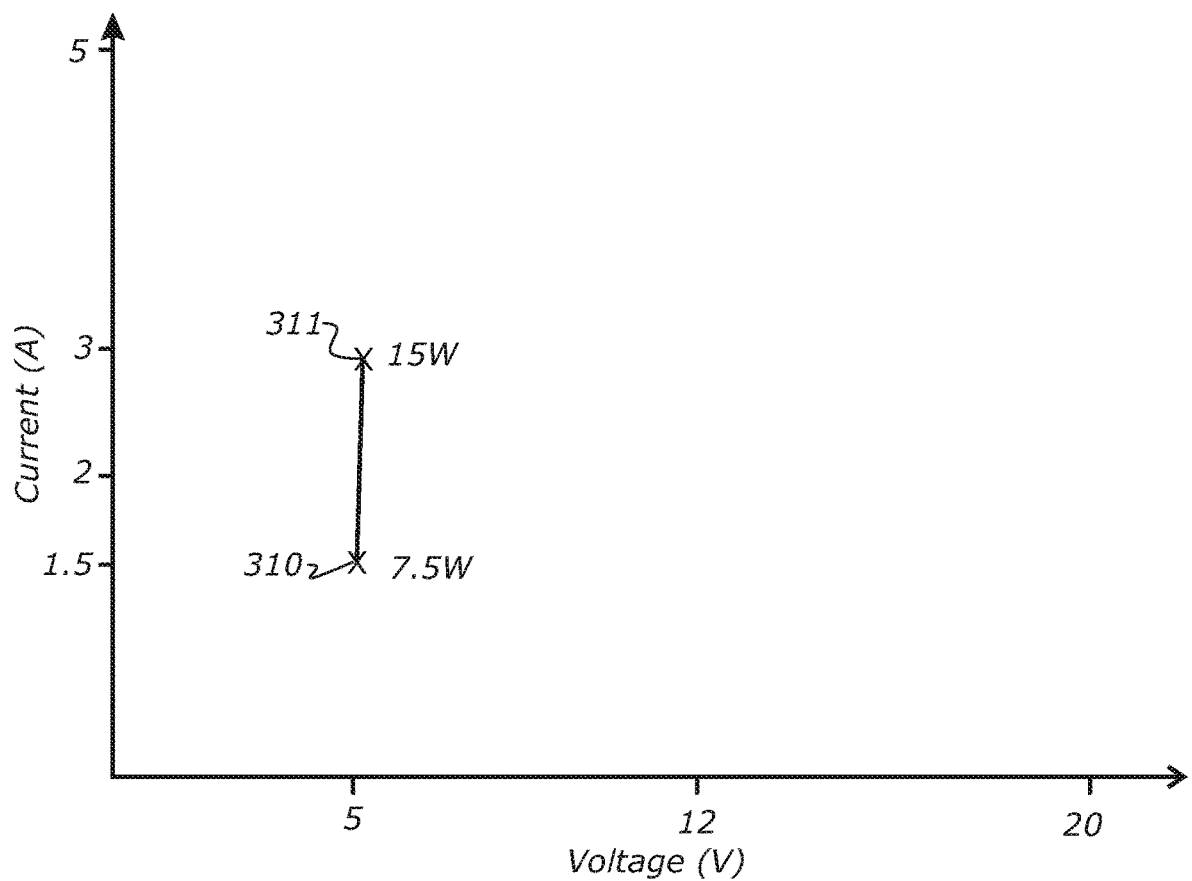
FIG. 4b shows the power configurations available with the USB-C power specification.

In the case of a USB-C connection 131, FIGS. 4a-4g show the power specifications of USB-C and USB-PD that a CPAP apparatus would need to be modified to meet. FIG. 4b shows the power profile according to USB-C power specification, while FIGS. 4c-4g show the power profiles available in the USB-PD power specification. These figures show that there are a limited number of ways of configuring power reception in the CPAP apparatus 10, and that the major obstacle in realizing this invention is configuring the power input of the CPAP apparatus 10 to receive power according to at least one of the disclosed power profiles.

To develop a CPAP apparatus 10 capable of receiving power through the preferred embodiment of the USB connection, the power specification or power profiles, disclosed in FIGS. 4b-4g, that the CPAP apparatus 10 will operate to must first be determined. The power specification or power profile that the CPAP apparatus 10 should receive power at may be determined, but not limited to, the following factors: voltage standard of rechargeable batteries, voltage rating of the mains power supply depending on the location CPAP apparatus 10 is operating in, acceptable current and power rating specified in healthcare devices in the relevant retail market, etc.

Following the determination of the power specification or power profile that the CPAP apparatus 10 should receive power at, the CPAP apparatus 10 needs to be redesigned so that its maximum and/or overall power consumption does not exceed the current and voltage rating specified by the power specifications disclosed above. It is envisaged that the CPAP apparatus 10 could modified in any manner that this is likely to be achieved. Various reductions in power consumption can then add up to a significant amount that would allow a CPAP apparatus 10 to operate to a power specification that can be provided by a USB-C cable 133 built to either a USB-C or USB-PD power specification.

As the development of USB standards are an ongoing process, it is anticipated that future power specifications with greater power, current or voltage rating will be released, and can be applied in a cable with a USB-C connector, or any other USB type connector, or other USB peripheral. This will reduce the burden for a person skilled in the art to find ways to reduce the CPAP power consumption. In such a situation, a person skilled in the art would only have to reduce CPAP power consumption by a smaller margin, or make fewer modifications for the device to conform to USB power specifications with a greater power rating.

1.3. USB Connection

The CPAP apparatus 10 is adapted to work with a USB connection 30 that carries sufficient power to meet the power requirements of the CPAP apparatus 10. A USB connection 30 comprises one or more USB specifications.

Each USB specification defines one or more of the following: shape of the physical connection, speed of data transfer, or voltage and current rating of the cable. USB specifications are not mutually exclusive, and in some cases may be used in conjunction with other specifications. For example, a USB connection 30 may comprise a USB cable 33, containing a USB-C connector 144 attached at both ends of the cable. The USB cable 33 may be adapted to transfer data at a rate specified by USB 3.1 specification, and also be adapted to transfer power specified by the USB-PD specification.

In this specification, a USB connection 30 refers to any USB-derived connection configuration capable of supplying power to the CPAP apparatus 10 and comprises the following: connector shape, conductor type and the power specification that the conductor is adapted to transfer power, or a combination thereof.

The connector attached at both ends of the USB connection 30 determines what port or socket the USB connection 30 can be plugged into. For example if a CPAP 10 comprises a USB-C port, then a USB connection 30 with a USB-C connector 144 is required to mate with the USB-C port 41 built into the CPAP apparatus 10. Each USB connector type is prescriptive about the pin wiring within the connector, what signal each pin transceives, and where the pin should be positioned within the USB connector.

The conductor type of the USB connection 30 refers to the medium in which the USB connection 30 conducts either a power and/or data signal. Existing methods include using a cable, flash drive, or a smart stick, although future alternatives may be envisioned, such as a USB smart stick capable of transceiving power and data signals wirelessly.

As mentioned above, the connector shape and pin configuration is specific to each USB connector type and the USB conductor medium must be configured specifically according to the requirements of the USB connector type so that all signals from each conducting pin of the connector are conducted through the conductor. USB connectors of different types cannot be interchanged and swapped at the ends of the USB conductor as the conductor configuration would no longer match up with the pins in the interchanged USB connector.

For the purposes of this invention, the preferred embodiment of the USB connection 30 is a cable with USB-C connectors 144 attached or adjacent to at least a first and/or second end of the cable, adapted to transfer power bidirectionally according to either a USB-C or USB-PD specification. Optionally, the data transfer capabilities of a USB-C specification cable may be utilised to provide information relating to CPAP power consumption and transceive data signals to control and regulate power usage within the CPAP apparatus 10.

Various USB connections 30 that could be used to supply power to the CPAP apparatus 10 as disclosed will now be described.

1.3.1 Physical Attributes of USB-C Connector and Cable

Figure 2A:
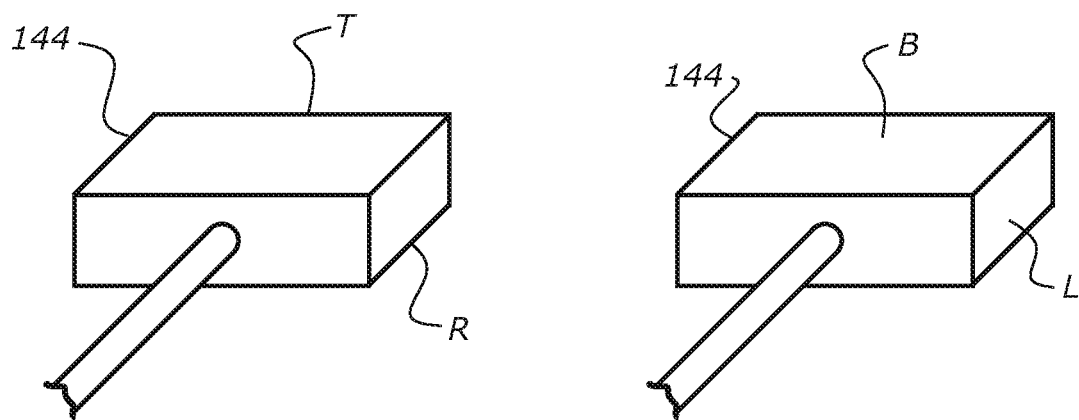
FIG. 2a shows a USB-C connector being plugged in, both in it's upright and upside down orientation.
Figure 2B:
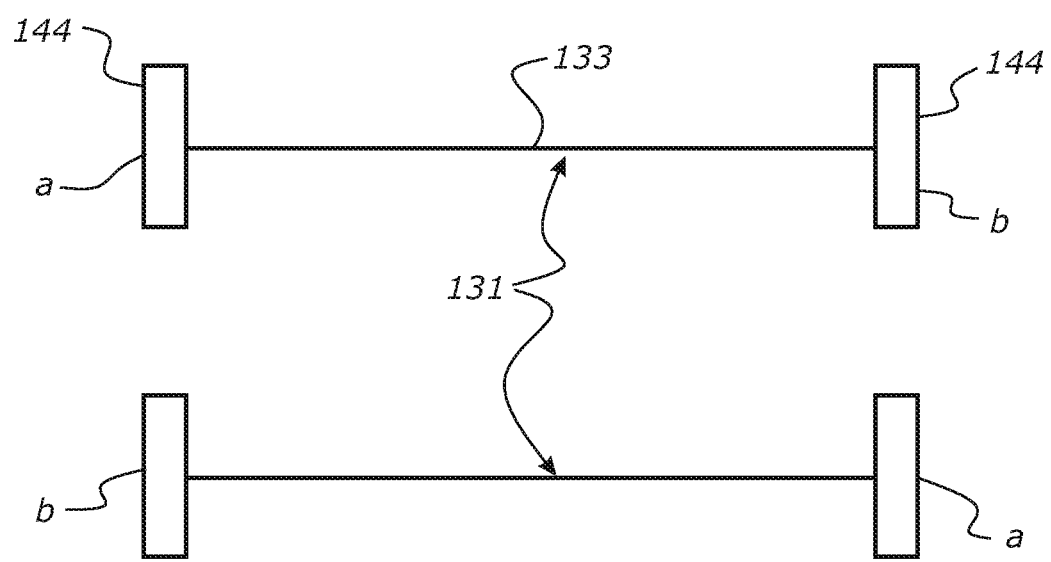
FIG. 2b shows a USB-C cable being plugged at both ends, irrespective of direction.

In one option, the USB-C connection 131 comprises a USB-C connector 144 attached to at least one end of a cable 133, as shown in FIGS. 2a and 2b. In the USB-C specification, the cable connectors 144 and its receptacle socket contain a port measuring approximately 8.3 mm by 2.5 mm. The cable plugs and receptacles are adapted for a rotatable orientation, allowing the connector 144 to mate in either an upright or upside down orientation, as shown in FIG. 2a. Both ends of the cable 133 have the same connector 144, allowing the cable 133 to be plugged in reverse order, shown in FIG. 2b. The maximum cable 133 length is preferably 2 m to avoid standing wave interference caused by the alternating current. A USB-C cable 133 contains EMI and RFI shielding to mitigate the effects of interference from proximate cables. Methods of mitigating interference can be implemented by any suitable means, including twisted pair, or an aluminium encasing of the wires.

As an alternative to cables 133, other methods of conducting power through the USB-C connection 131 may be used. For example, albeit not limited to the following, a USB stick or peripheral may be used to transfer power to and from the CPAP apparatus 10. As another example, future technological improvements may permit power to be transceived wirelessly between a power supply 20 and the CPAP apparatus 10 via a USB stick or peripheral plugged into the CPAP apparatus 10.

1.3.2 Examples of USB-C Connector and Cable

This section will describe several examples of the preferred embodiment of the USB-C connection 131. The described examples all comprise a cable 133 for transferring power to the CPAP apparatus 10, with at least one end containing a USB-C connector 144. The examples can be broadly categorised into two groups: tethered cables and non-tethered cables. These descriptions are non-limiting and any other applicable use of a USB-C connection 131 may be applied to a CPAP apparatus 10.

1.3.2.1 Tethered Cables

Tethered cables integrate the connector and plugs at the ends of the cable into a single item so that it is ready to use and no self-assembling is required by the user. Tethered cables comprise a first USB-C connector 144 attached or adjacent to at least the first end of the cable, while a second end of the cable is directly connected to a USB enabled component, such as for example a power supply battery pack.

Figure 3A:
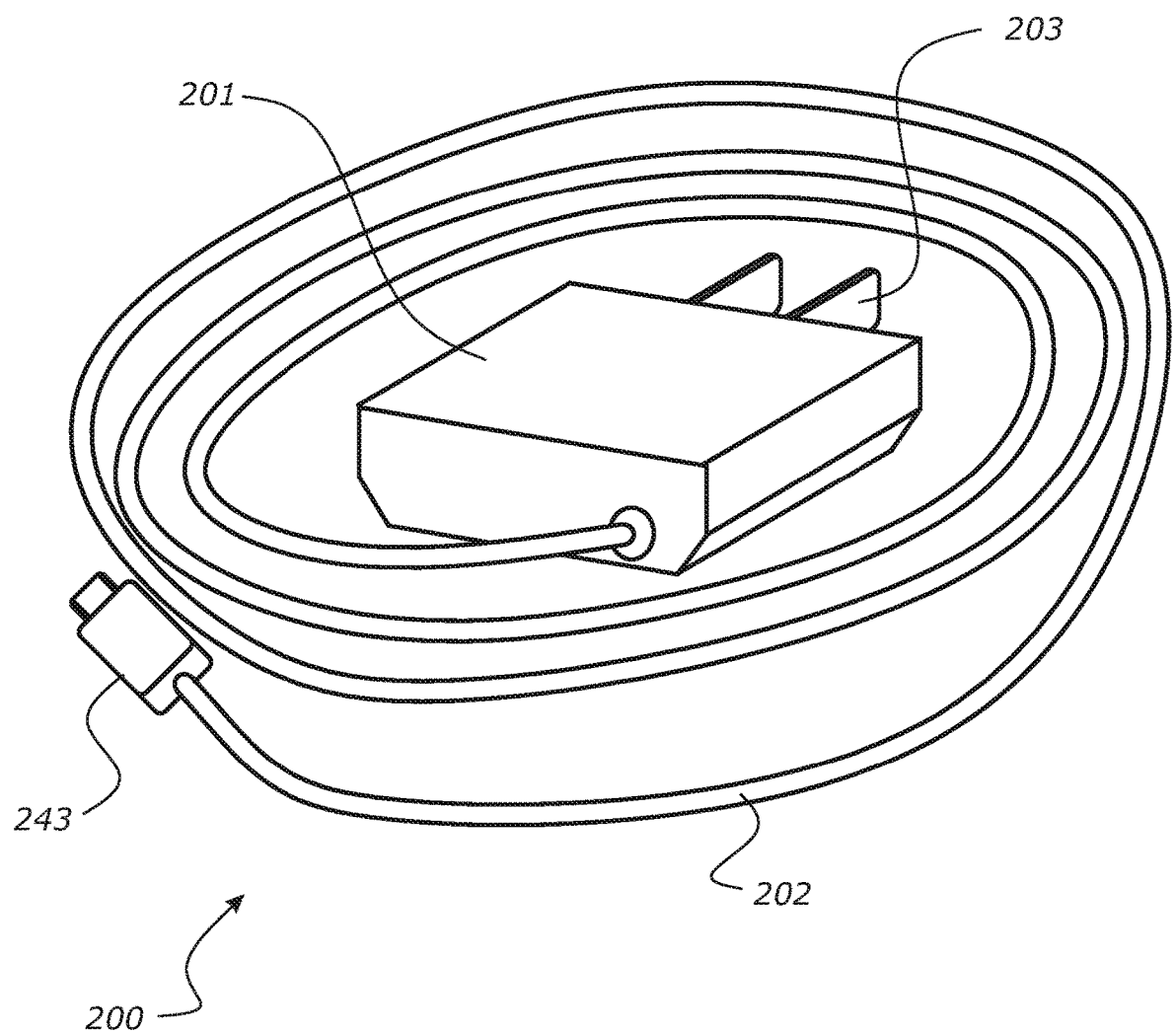
FIG. 3a shows a power adapter as a first application for a tethered USB-C connector.

A first application 200 for tethered USB-C connector is a power adapter 201 with a lead 202 and plug 203 for an inlet, as shown in FIG. 3a. A USB-C connector 243 is placed at the distal end of the lead 202.

Figure 3B:
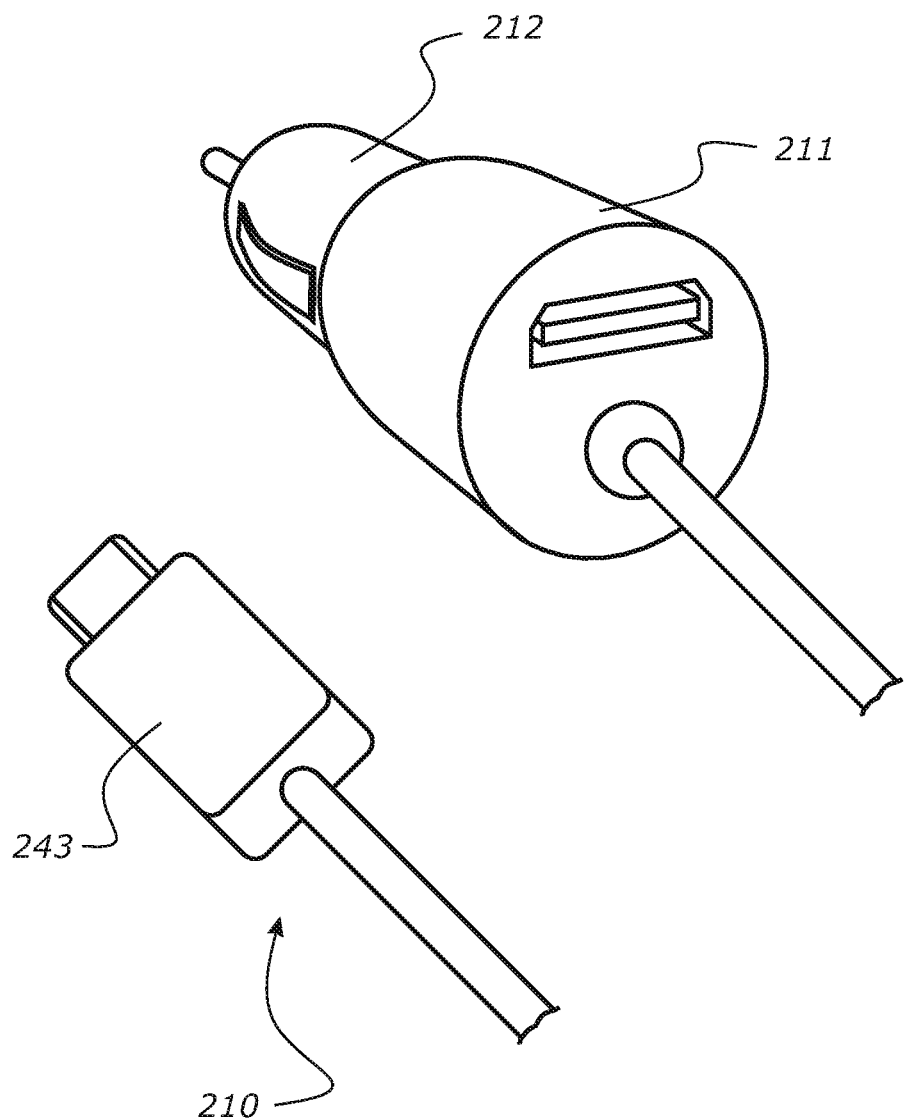
FIG. 3b shows a power adapter plugged into a car cigarette lighter as a second application for a tethered USB-C connector.

A second application 210 for tethered USB-C connectors is a power adapter 211 that can be connected to a car power adapter (cigarette lighter) 212, as shown in FIG. 3b.

A third application for tethered USB-C connectors is a battery pack (e.g. a lithium ion battery pack) with a socket for charging.

It will be appreciated that other configurations are possible, including having the cable tethered to the CPAP with a USB connector at the distal end of the cable for connection to a USB connector on a power source.

1.3.2.2 Non-Tethered Cables

Non-tethered cables make all cable-related components modular in nature, rather than a fixed single item, such as tethered cables. This allows the user to disconnect a cable from a first power adapter and connect it to a second power adapter adapted for use in another country with a different plug connection to the power mains.

Figure 3C:
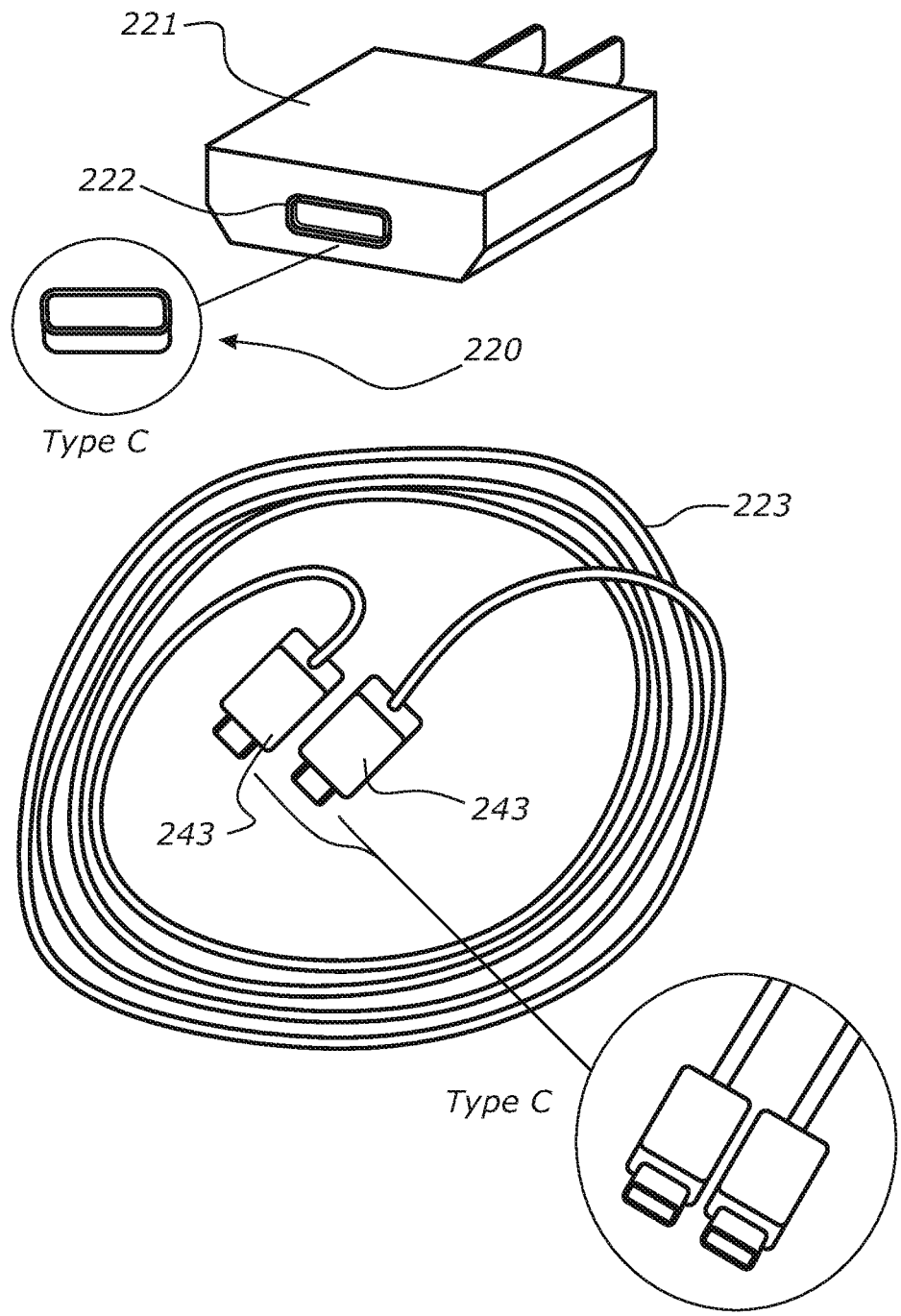
FIG. 3c shows a power adapter as a first application for a non-tethered USB-C connector.

A first application 220 for a non-tethered USB-C connector is a power adapter 221 with an outlet socket 222 that enables the insertion and removal of the USB-C cord 223, as shown in FIG. 3c. A USB-C connector 243 is placed at both ends of the USB-C cord 223.

Figure 3D:
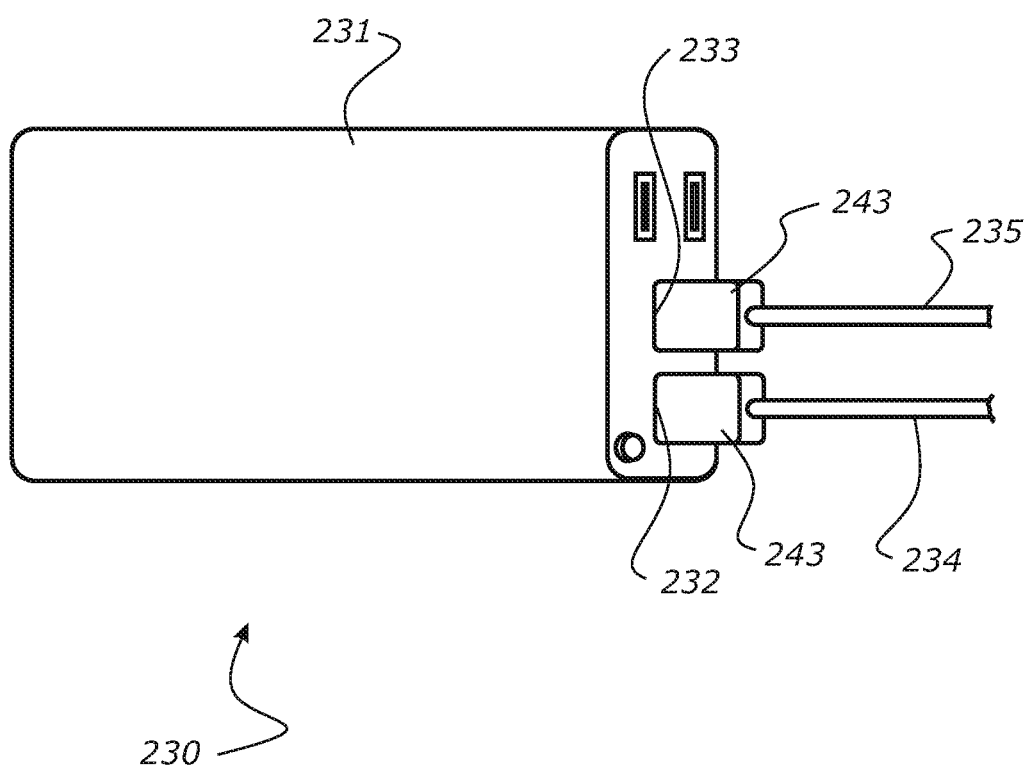
FIG. 3d shows a battery pack as a second application for a non-tethered USB-C connector.

A second application 230 for a non-tethered USB-C connector is the use of the technology in a portable battery pack 231, as shown in FIG. 3d. The battery pack can include more than one (for example two) USB-C ports 232, 233. A first port 232 can be used to connect a cable 234 between a CPAP apparatus 10 and the battery pack 230, to power the CPAP apparatus 10. A second port 233 can be used to connect the battery pack 231 via cable 235 to a charging power supply (i.e. through the use of a power adapter previously described). The battery pack 231 can therefore be charged with simultaneous use of the battery pack 231 to power a CPAP apparatus 10 as a 'feed-through system'. Such a configuration forms a UPS (uninterruptible power supply) type power supply. Alternatively the battery pack 231 can be charged while the CPAP apparatus 10 is not in use or is not plugged via a USB-C cable 234 to the battery pack 231. In other configurations, the feed-through system can have power supplied from a car battery, a car power adapter or another power supply. Additional applications could see the device powered from multi-purpose power banks, as opposed to specifically designed power banks.

Figure 3E:
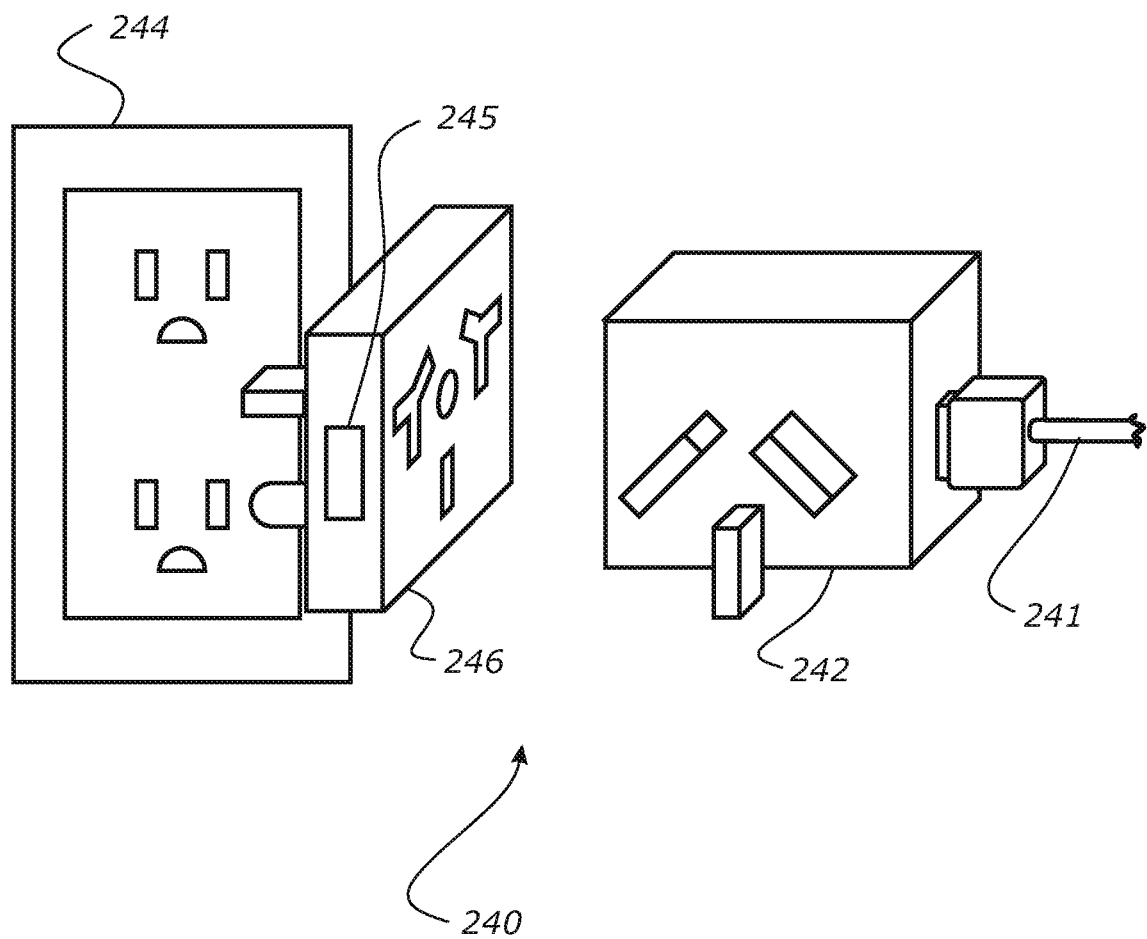
FIG. 3e shows a universal power adapter as a third application for a non-tethered USB-C connector.

A third application 240 for a non-tethered USB-C connector is the use of a USB-C cord 241 with varying mains power connections, dependent on the country that one is using the device in. FIG. 3e depicts an example of this, where a USB-C cable 241 is plugged into a AS/NZS 3112 power adapter 242, which in turn is about to be plugged into a universal power adapter 246 plugged into a NEMA socket 244. Alternatively, the USB-C cable 241 can be plugged directly into the socket 245 built into the side of the universal power adapter 246.

1.3.2.3 Cableless USB Connection

It should be noted that a USB-C connection 131 can be formed without requiring a cable 133. In the case of the tethered and non-tethered cable applications disclosed, appropriate modifications can be made so that a USB-connection 131 can be made without a using a cable to connect the CPAP device 10 to any part of the USB connection 131 and/or power supply 20.

For example, the second application of the non-tethered cable example disclosed in FIG. 3c can optionally be modified so that the battery pack 230 directly couples the CPAP device 10 via a USB-C connector 144 embedded in the battery pack 230, thereby excluding cable 234 and the first port 232 from its design.

1.3.3 USB Power Specification

In a USB-C power specification, a peak power of up to 15 W (5V and 3 A) can be transmitted. A cable 133 with USB-C connectors 144 may be used in conjunction with a USB-PD (power delivery) specification, to deliver a peak power of up to 100 W (20V and 5 A). It is anticipated that future versions and revisions of USB-C and USB-PD specifications may also be used in this invention to deliver power to a CPAP apparatus 10. It is anticipated that power specifications released in the future will comprise greater power limits than what currently is prescribed in the USB-C and USB-PD specifications. This will ease the burden of finding ways to reduce peak power consumption of the CPAP apparatus 10. Electronic marking (EMCA) may be used if a current in excess of 3 A is needed to power the CPAP apparatus 10.

The preferred embodiment of the USB connection is adapted to operate to a USB-C or USB-PD specification, with their configurations shown graphically in FIGS. 4a-4g. These power specifications are higher compared with their predecessors, which eases the task of minimising peak power requirements of the CPAP apparatus 10, so that its power requirements do not exceed USB power specifications.

At a low power setting, USB-C has a power configuration 310 of 1.5 A and 5V, providing a maximum power of 7.5 W. At a high power setting, USB-C has a power configuration 311 of 3 A and 5V, providing a maximum power of 15 W. The power profile of the USB-C power specification is graphically shown in FIG. 4a.

As the USB-PD power specification involves transferring high power over a standard cable or through other types of electrical conductors, it is important that power gradually ramps up or down in a safe manner. The power profiles specified according to the USB-PD power specification divides the process of switching between an 'off' and 'on' state (or vice versa) into a stepped progression. For example, a USB-C cable 133 built according to the USB-PD power specification can transfer between 10 W and 100 W by either stepping up or stepping down, with each step roughly doubling or halving the power from the previous step.

USB-PD comprises 6 power profiles (shown in Table 1 on FIG. 5, and FIGS. 4b-g), with a power specification limit of 5 A and 20V, providing a maximum power limit of 100 W. A cable with a USB-PD specification can transfer power according to at least one of the six specified profiles.

Profile 0 is currently allocated with a 'reserved' status, and no definite values are assigned to it at this point. For this reason, USB cables and USB devices built to the USB-PD power specification do not operate according to this particular profile in practice.

Figure 4C:
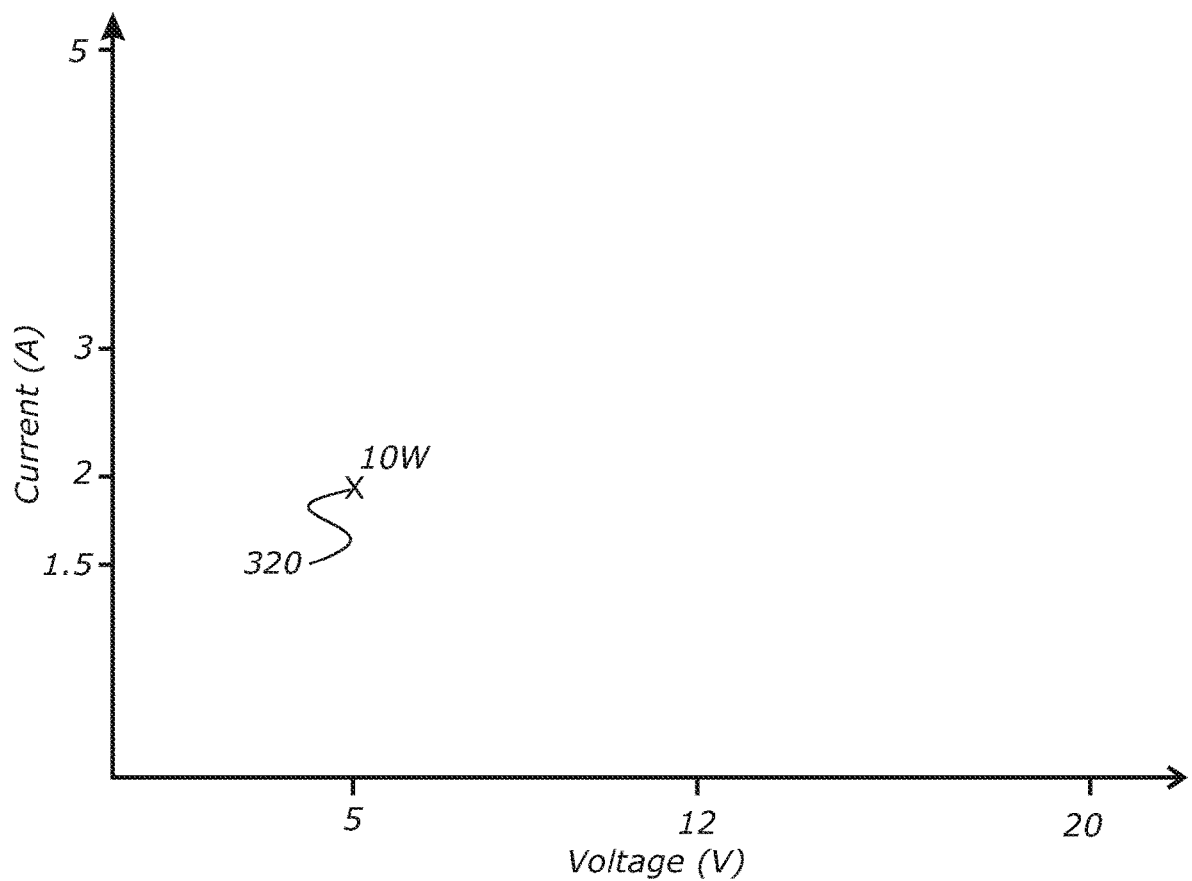
FIG. 4c shows the power configurations available for power profile 1, within the USB-PD power specification.

FIG. 4c shows the configuration available for profile 1. One configuration 320 exists in this profile, with a voltage rating of 5V and a current rating of 2 A, producing a power rating of 10W.

Figure 4D:
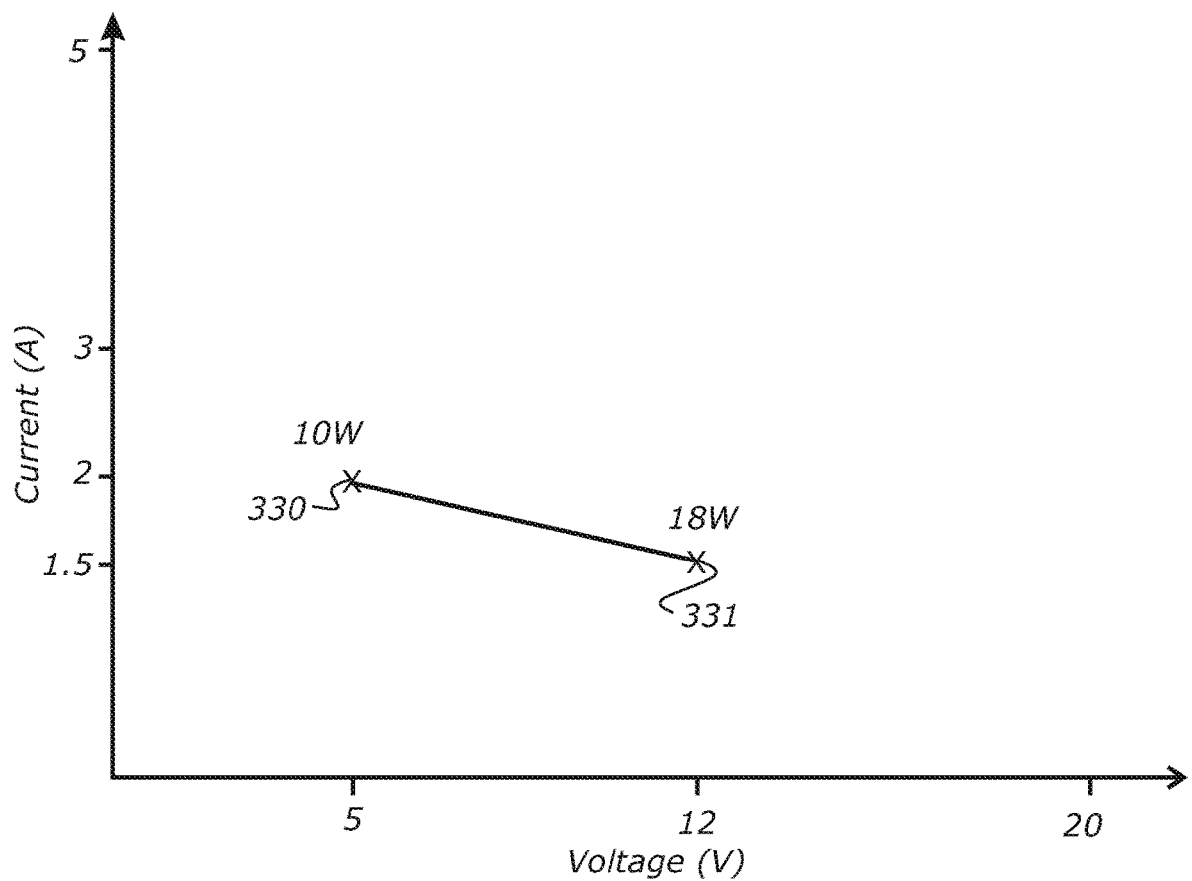
FIG. 4d shows the power configurations available for power profile 2, within the USB-PD power specification.

FIG. 4d shows the configurations available for profile 2. Two configurations 330, 331 exist in this profile. The first configuration 330 has a voltage rating of 5V and a current rating of 2 A, producing a power rating of 10 W. The second configuration 331 has a voltage rating of 12V and a current rating of 1.5 A, producing a power rating of 18 W.

Figure 4E:
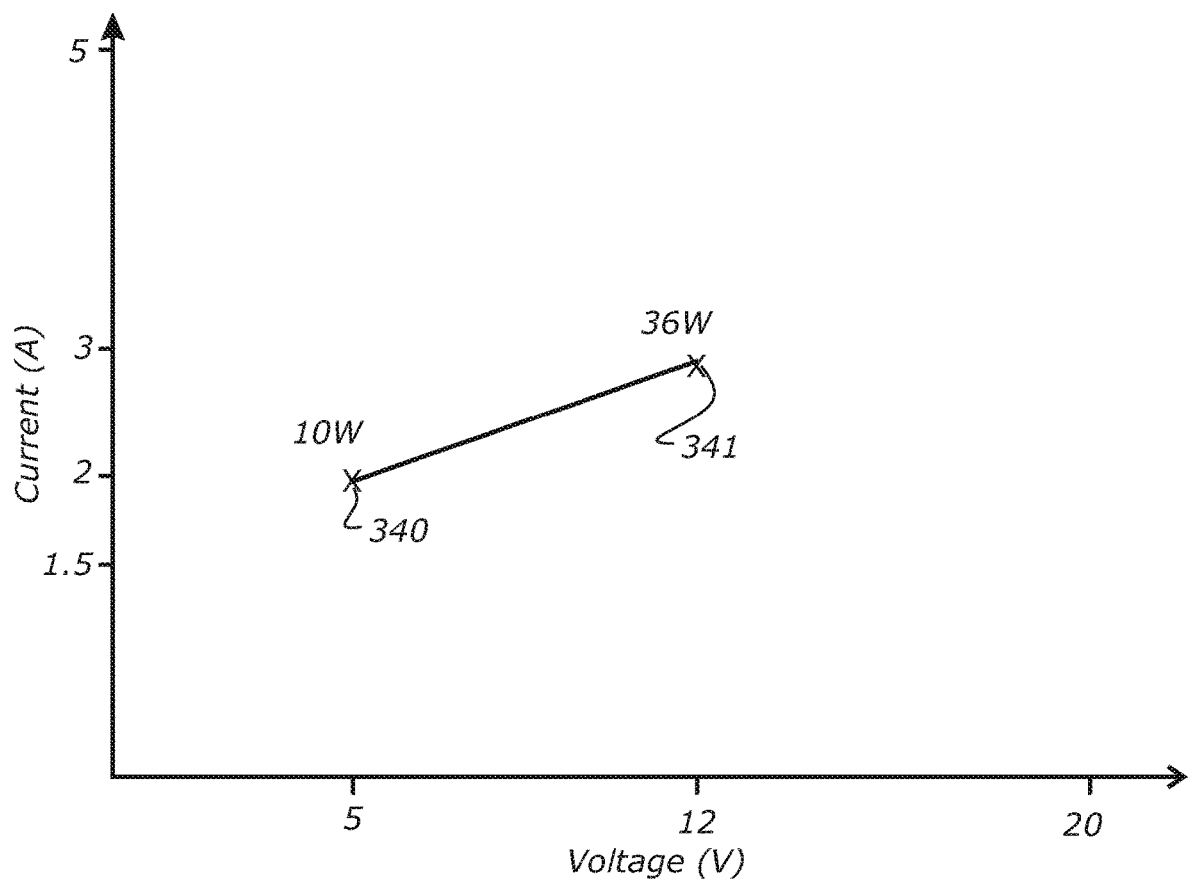
FIG. 4e shows the power configurations available for power profile 3, within the USB-PD power specification.

FIG. 4e shows the configurations available for profile 3. Two configurations 340, 341 exist in this profile. The first configuration 340 has a voltage rating of 5V and a current rating of 2 A, producing a power rating of 10 W. The second configuration 341 has a voltage rating of 12V and a current rating of 3 A, producing a power rating of 36 W.

Figure 4F:
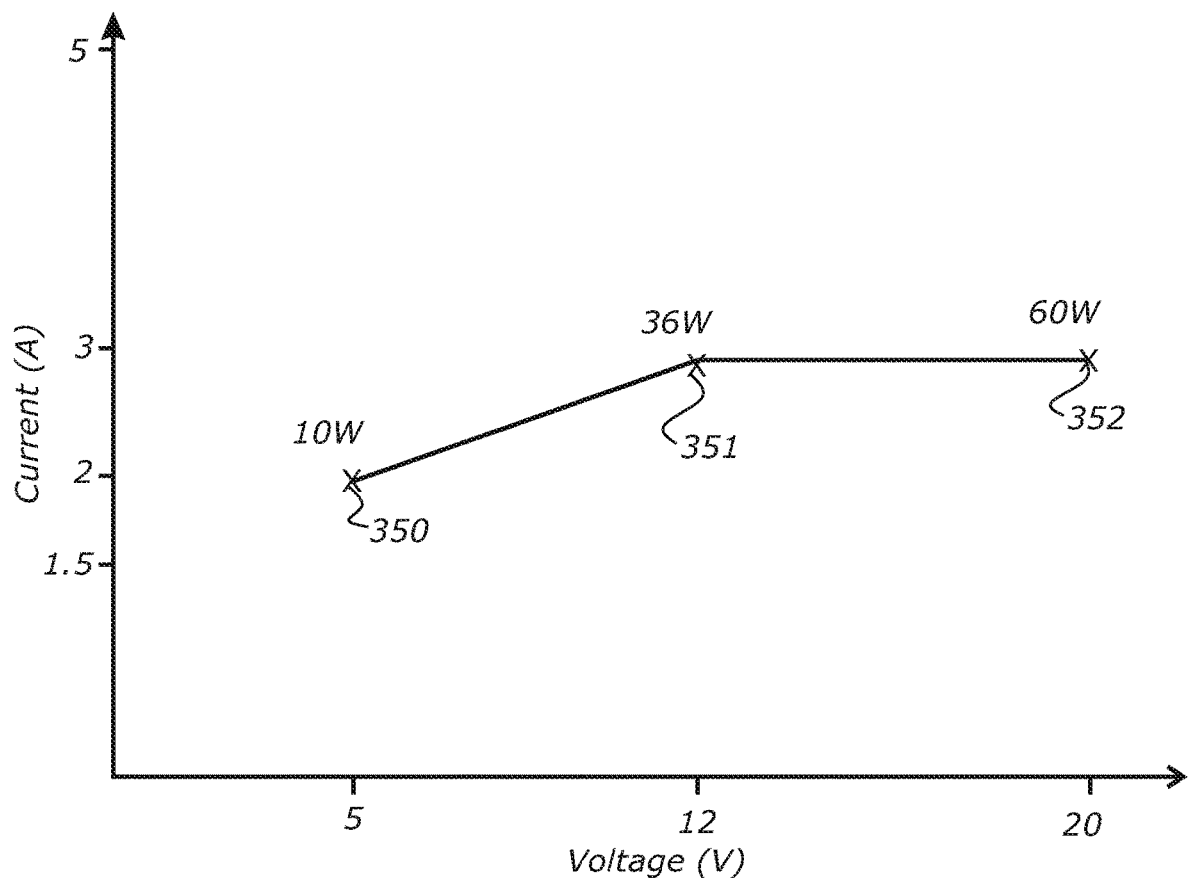
FIG. 4f shows the power configurations available for power profile 4, within the USB-PD power specification.

FIG. 4f shows the configurations available for profile 4. Three configurations 350, 351, 352 exist in this profile. The first configuration 350 has a voltage rating of 5V and a current rating of 2 A, producing a power rating of 10 W. The second configuration 351 has a voltage rating of 12V and a current rating of 3 A, producing a power rating of 36 W. The third configuration 352 has a voltage rating of 20V and a current rating of 3 A, producing a power rating of 60 W.

Figure 4G:
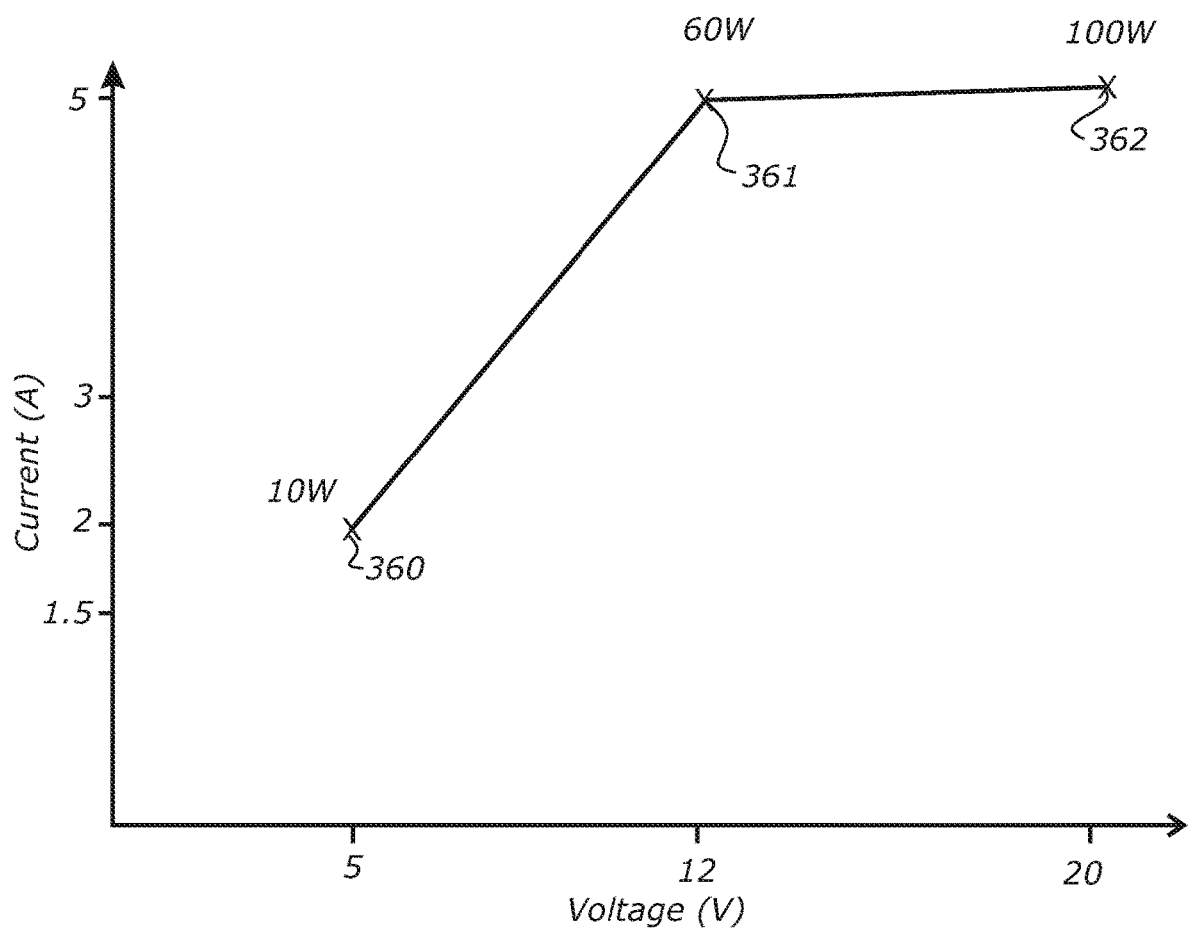
FIG. 4g shows the power configurations available for power profile 5, within the USB-PD power specification.

FIG. 4g shows the configurations available for profile 5. Three configurations 360, 361, 362 exist in this profile. The first configuration 360 has a voltage rating of 5V and a current rating of 2 A, producing a power rating of 10 W. The second configuration 361 has a voltage rating of 12V and a current rating of 5 A, producing a power rating of 60 W. The third configuration 362 has a voltage rating of 20V and a current rating of 5 A, producing a power rating of 100 W.

The scope of USB power specifications is not limited to the disclosure above, and it is important to note that future revisions or versions of USB-PD or USB-C power specifications in particular may be released.

1.3.4 Data Transfer Capabilities

USB-C connections 131 are capable of transmitting signals over a wide frequency bandwidth, and can therefore transfer large quantities of data at a fast rate. A USB-C connection 131 may transfer data at a rate specified by an existing USB specification, depending on the devices that the USB-C connection 131 is connected to, and the maximum data transfer speed achievable in both devices.

USB-C connections 131 support existing USB specifications, including USB 3.1 Generation 1 and Generation 2, USB 3.0 as well as USB 2.0. It is anticipated that future USB specifications prescribing data transfer speeds may also be implemented with USB-C connections 131 and may be used in this invention.

EMCA may be used if the USB 3.1 Generation 2 specification is used in the USB-C cable 133 to transfer data to and from the CPAP apparatus 10.

The data transfer rates disclosed define each USB specification listed. USB 1.x is defined with a theoretical data transfer rate of up to 1.5 Mbit/s. This specification is rarely used, as data transfer rate is relatively slow in comparison with its successors. USB 2.0 is defined with a theoretical data transfer rate of up to 480 Mbit/s. USB 3.0 is defined with a theoretical data transfer rate of up to 5 Gbit/s. USB 3.1 is defined with a theoretical data transfer rate of up to 10 Gbit/s.

The data transferring ability of the USB-C connection 131 may assist in co-ordinating power consumption and conservation, as explained in the next section.

1.4. Power Supply

The CPAP apparatus 10 can be connected via a USB-C connection 131 to receive power from the mains supply. The power specification of the mains supply is preferably 230V, 50 Hz or 120V, 60 Hz. However a lower voltage suitable for inputting into a CPAP apparatus 10 may also be used.

A power supply 20 carrying a different voltage or frequency rating may also be converted using a power adapter or converter.

The communication link in the cable 133 can be used as a feedback mechanism or to supply real-time data. This added enhancement can be applied in this invention to protect the CPAP apparatus 10 from a power surge, or to regulate the amount of power being supplied to the device from the power supply 20.

For example, if the CPAP apparatus 10 detects a power surge event (either detected from internal circuitry, or by receiving a warning from the communication link in the cable 133), the CPAP apparatus 10 can transmit a signal over the USB-C cable 133 to the power supply 20 to stop supplying power. The controller 50 in the CPAP apparatus 10 can disengage the power module 90 from receiving power from the USB-C connection 131, and activate the backup power supply. Once the power surge event is over, the CPAP apparatus 10 can relay a signal through the USB-C connection 131 to the power supply 20 to resume the supply of power from an external source.

Optionally, in a smart grid application, the USB-C connection 131 may be used to supply power back to the grid. The communication link in the USB-C cable 133 can be used to co-ordinate the redistribution of power in this instance, either supplying power to the CPAP apparatus 10, or reversing the direction of power when required.

The CPAP apparatus 10 can be connected to a portable power source, such as an external battery pack 230, to transmit power and communication signals to the CPAP apparatus 10. Power may be transferred from the portable power source to the CPAP apparatus 10, depending on how much power is left in the portable power source. If the portable power source is running low on reserves, the communication link in the USB-C connection 131 can be used to transmit a signal to the CPAP apparatus 10 to lower power output and conserve energy.

2. Dual Power Supply Embodiment

Figure 6:
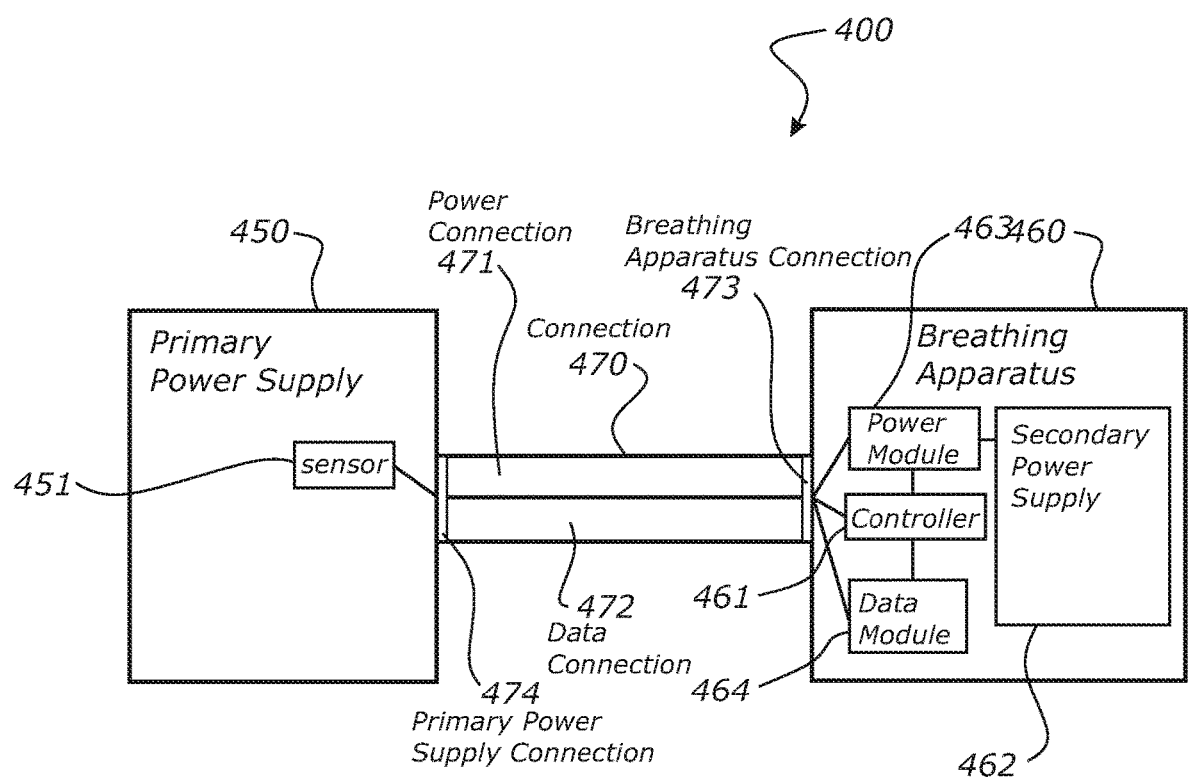
FIG. 6 shows a second block diagram of a breathing apparatus (with an internal power supply) connected to a primary power supply via a power and data connection.

In another embodiment, with reference to FIG. 6, the present invention may also be said to comprise a respiratory therapy system 400 comprising a primary power supply 450, a breathing apparatus 460, and a connector 470 that forms a connection between the primary power supply 450 and the breathing apparatus 460. The breathing apparatus 460 comprises a controller 461, and a secondary power supply 462. The breathing apparatus 460 therefore has at least two sources of power: the primary power supply 450, and the secondary power supply 460. Having more than one power source can improve reliability. If there is a fault with either, the alternative power supply can be drawn from to provide an uninterruptible power supply to the breathing apparatus 460, which reduces the risk of the breathing apparatus 460 experiencing power failure, or a sustained power failure. This helps maintain continuity of operation of the breathing apparatus 460.

The connector (also referred to as connection herein) 470 comprises a power connection 471, and a data connection 472. The power connection 471 is configured to transfer power bi-directionally, and the data connection 472 is configured to transfer data bi-directionally. Each direction of the bi-directional power connection 471 and data connection 472 is independently controllable from the respective other direction. This configuration facilitates the supply of power from the primary power supply 450 to the breathing apparatus 460, and also facilitates the transfer of data to and from the breathing apparatus 460. The primary power supply 450 can comprise a mains electric power supply (for example including a wall power outlet), a device to convert energy supplied by the mains electric power supply to a state suitable for use with the breathing apparatus 460 (for example a transformer), a portable electric power supply (for example a portable battery), or a combination thereof.

The controller 461 is configured to monitor the primary power supply 450. The controller 461 can also monitor the breathing apparatus 460. In at least one configuration, the controller 461 is configured to control the operation of the breathing apparatus 460. The controller 461 is configured to determine when the breathing apparatus 460 should be powered by the primary power supply 450, and determine when the breathing apparatus 460 should be powered by the secondary power supply 462. For example, the breathing apparatus 460 may be configured to receive power from the primary power supply 450 by default to power breathing apparatus 460 components such as a flow generator and/or other components when the primary power supply 450 is connected to the breathing apparatus 460. Alternatively, the breathing apparatus 460 may be configured to receive power for the flow generator and other components from the secondary power supply 462 by default, and the primary power supply 450 may be configured to provide power to the secondary power supply 462 (for example, as a source of energy to charge the secondary power supply 462 if the secondary power supply 462 is a battery).

If the primary power supply 450 overheats, or the controller 461 detects a power fault in the primary power supply 461, or the connection 470 is disconnected from the primary power supply 450 or breathing apparatus 460, or the primary power supply 450 is disconnected from the wall power outlet, the controller 451 may relay instructions so to cease receipt of power to the breathing apparatus 460 from the primary power supply 450. This might occur because while the controller 461 is monitoring a parameter of the primary power supply 450, the controller 461 determines that the monitored parameter differs from a parameter threshold. At this point, the controller 461 instructs the breathing apparatus 460 to disengage from the primary power supply 450 so that the primary power supply 450 no longer supplies power to the breathing apparatus 460. This can prevent damage to the breathing apparatus 460. The controller engages the secondary power supply 462 on disconnection of the primary power supply 450. This can ensure the breathing apparatus 460 can continue operating without interruption. This can ensure that an uninterrupted supply of power is provided to the breathing apparatus 460. In an alternative configuration, the controller can engage the secondary power supply 462 prior to disconnection of the primary power supply 450. This can ensure the breathing apparatus 460 can continue operating without interruption. This can ensure that an uninterrupted supply of power is provided to the breathing apparatus 460.

The controller (circuitry) used to isolate the primary power supply 450 is in the breathing apparatus 460 instead of the primary power supply 450. This leads to a reduced number of components in the primary power supply 450 and/or provides simplicity of the circuitry in the primary power supply 450, therefore reducing the size of the primary power supply 450 as well as reducing manufacturing costs of the primary power supply 450. Reducing the number of components and/or increasing the simplicity of the design of the primary power supply 450 can also decrease its failure rate or increase its useful life.

2.1. Breathing Apparatus

Further embodiments and/or variants of the disclosed present invention will now be discussed herein in greater detail, with reference to FIG. 6.

A breathing apparatus 460 is configured to provide respiratory therapy, such as, but not limited to, CPAP therapy. The breathing apparatus 460 may provide nasal high flow (NHF) therapy, non-invasive ventilation therapy, or a combination of the mentioned therapies when an appropriate mode is selected. For example the breathing apparatus 460 may include a first mode in which it is configured to deliver a first respiratory therapy (for example CPAP therapy), and a second mode in which it is configured to deliver a second respiratory therapy (for example NHF therapy).

The breathing apparatus 460 comprises a controller 461. The controller 461 may optionally be an electromechanical controller or processor, or alternatively, the controller 461 could be a microprocessor. Alternatively, the controller 461 could include an electro-mechanical relay.

The breathing apparatus 460 comprises a secondary power supply 462. Preferably the secondary power supply 462 is an internal battery. Alternatively, the secondary power supply can be an external battery. The external battery may be configured to be mounted onto a side of the breathing apparatus 460 and provide power when mounted. In some situations, the respiratory therapy system 400 may be configured such that the primary power supply 450 charges the internal battery when the battery is not charged to full capacity and the primary power supply 450 is engaged.

The breathing apparatus 460 preferably comprises a power module 463 for controlling power distribution, and also preferably comprises a data module 464 configured to transmit to and receive data from the primary power supply 450 via the connection 470. In some situations the breathing apparatus 460 include a circuit that includes the controller 461, power module 463, and data module 464.

The power module 463 can act as a power switch to provide, direct and/or distribute power to the rest of the breathing apparatus 460. The power module 463 is instructed by the controller 461 to switch the source of power to be used by the breathing apparatus 460 from the primary power supply 450 or from the secondary power supply 462. Alternatively, the power module 463 can act independently to switch the source of power to be used by the breathing apparatus 460 from the primary power supply 450 or from the secondary power supply 462. Preferably the controller 461 is configured to monitor a parameter of the primary power supply 450, and disengage the power module 463 from the primary power supply 450 if the parameter differs from the parameter threshold. In some situations the parameter monitored by the controller 461 may be a deviation from a predetermined value. In some situations, the monitored parameter may exceed an upper parameter threshold. In some situations, the monitored parameter may be under a lower parameter threshold. Preferably, the controller 461 is configured to engage the power module 463 with the secondary power supply 422 on disconnection of the primary power supply 450 such that the uninterrupted supply of power is provided to the breathing apparatus 460. In some situations, the power module 463 is disengaged from the primary power supply 450 if the parameter exceeds the parameter threshold. In some situations, the power module 463 is disengaged from the primary power supply 450 if the parameter is less than the parameter threshold. In some situations, the power module 463 is disengaged from the primary power supply 450 if the parameter is equal to the parameter threshold.

2.2. Primary Power Supply

The primary power supply 450 is an external power source for providing power to the breathing apparatus 460. The primary power supply 450 is configured to connect 470 to the breathing apparatus 460. Preferably the primary power supply 450 comprises a device for converting electrical energy supplied by a mains electric power supply to a state suitable for use with the breathing apparatus 460, such as a "smart" power brick comprising a transformer for example. The power brick can be considered "smart" as it includes functionality in excess of simply acting as a source for converting power from a first form (such as electricity at standard residential specifications) to a form usable by the breathing apparatus 460 (for example, direct current (DC)). This can include the power brick comprising a sensor to sense and/or report sensor data.

In one example of the primary power supply 450 may be the battery pack 230 as shown in FIG. 3*d*. In at least one configuration, the battery pack 230 can provide a standalone source of power, by supplying power to the breathing apparatus 460 via connector 234. In another configuration, the battery pack 230 can receive power from the mains power supply (or other external power source) via connector 235 in order to power the breathing apparatus 460 via connector 234. The battery 231 can optionally be recharged so that the battery pack 230 can function as a standalone power source if needed.

Preferably the primary power supply 450 includes a sensor 451. Preferably the sensor 451 is powered by at least the primary power supply 450. The sensor 451 can provide sensor data to the controller 462 for monitoring purposes to determine the status of the primary power supply 450. The sensor data can be used to determine whether the power module 463 should still engage with the primary power supply 450 for supplying power to the breathing apparatus 460.

2.3. Connection

The connector 470 is configured to facilitate transmission of power 471 and data 472 between the primary power supply 450 and the breathing apparatus 460. The multipurpose connector 470 is configured to transmit power 471 and data 472 bi-directionally, and preferably simultaneously. Each of the two connections 471 and 472 can operate independently of one another, and therefore each connection can be isolated individually.

Preferably, the connector 470 comprises an electrical cord. Preferably, the connector 470 comprises a breathing apparatus connection 473 on the breathing apparatus 460 configured to receive the electrical cord. In at least one embodiment, the breathing apparatus connection 473 is a breathing apparatus port. The port can be configured to receive a plug of the electrical cord. Preferably, the electrical cord is removable from the breathing apparatus connection 473. Preferably the breathing apparatus connection 473 is a USB port, and more preferably a USB-C port. Preferably the electrical cord is a USB cable, or more preferably a USB-C cable. Preferably, the primary power supply 450 includes a primary power supply connection 474. The primary power supply connection 474 can be a port. The port can be configured to receive a plug of the electrical cord. The primary power supply connection 474 is preferably a USB port or more preferably a USB-C port, and the connection 470 between the primary power supply 450 and the breathing apparatus 460 is a USB port or more preferably a USB-C connection via the USB/USB-C cable. Preferably the physical attributes and the power and/or data specifications of USB connector 470 and USB ports 473, 474 can be the physical attributes, power specification, or data specification of USB connections described in the earlier embodiment.

In at least one configuration, the connector 470 is configured to facilitate bi-directional, independently controllable power and data transfer between the breathing apparatus 460 and the primary power supply 450. The connector 470 comprises a first connector plug and a second connector plug. The breathing apparatus 460 comprises a breathing apparatus port 473. The primary power supply 450 comprises a primary power supply port 474. The first connector plug is configured to connect to the breathing apparatus port 473. The second connector plug is configured to connect to the primary power supply port 474. The primary power supply port 474. The breathing apparatus port 473 can also be of the same configuration as the primary power supply port 474. The connector 470 can be said to be orientation independent (the first and second connector plugs are interchangeably usable between devices 450 and 460). The connector 470 can be removably connectable to each of the breathing apparatus port 473, the primary power supply port 474.

In at least one configuration, the first connector plug is a male USB-C connector. In at least one configuration, the second connector plug is a male USB-C connector. In at least one configuration, the breathing apparatus connection 473 is a female USB-C connector (also known as a USB-C port). In at least one configuration, the primary power supply connection 474 is a female USB-C connector.

2.4. Method of Operation

The breathing apparatus 460 is configured to be powered from the primary power supply 450, but can also be powered by a secondary power supply 462 that can be contained in the breathing apparatus 460. It is envisaged that the breathing apparatus 460 is preferably powered by the primary power supply 450 by default. That is, when the primary power supply 450 is connected to the breathing apparatus 460 via the connection 470, the breathing apparatus 460 preferences sourcing power from the primary power supply. The external nature of the primary power supply results in it being more likely to be capable of providing a continuous supply of power to the breathing apparatus 460, for example sourced from an electrical grid. In contrast, the secondary power supply 462, such an internal battery for example, can only provide power to the breathing apparatus 460 for a limited period of time. For this reason, the secondary power supply 462 can be treated as an auxiliary power source that is used as an emergency back up when it is not possible to power the breathing apparatus 460 using the primary power supply 450, or when doing so could damage the breathing apparatus 460 due to malfunction of the primary power supply.

For example, if the breathing apparatus 460 detects a power fault in the primary power supply 450, or the primary power supply 450 overheats, it is desirable for the breathing apparatus 460 to shut down or disengage the supply of power from the primary power supply 450 to breathing apparatus 460 to prevent damage to the device, and to maximize the safety of the user. The breathing apparatus 460 is configured to determine whether to disengage the supply of power from the primary power supply 450 according to a set criteria, which will be discussed in detail later. It is also desirable that the breathing apparatus 460 continues to receive power, particularly when providing respiratory therapy to a patient. When the primary power supply 450 becomes unavailable, the breathing apparatus 460 is configured to engage the secondary power supply 462. Switching between the two power sources should be done in a manner that the breathing apparatus 460 can continue to function without interruption, or continues to receive an uninterrupted supply of power, and the breathing apparatus 460 maintains continuity of operation.

Therefore this dual power supply embodiment may also be considered to be a method of controlling a breathing apparatus 460. The disclosed method may comprise a step of monitoring a parameter of the primary power supply 450 and the breathing apparatus 460 configured to facilitate transmission 430 of power 471 and data 472 between the primary power supply 450 and the breathing apparatus 460. The disclosed method may also comprise determining that the monitored parameter differs from a parameter threshold. The disclosed method may also comprise disengaging a power module 463 of the breathing apparatus 460 from the primary power supply 450. The disclosed method may also comprise engaging the power module 463 with the secondary power supply 462 such that the breathing apparatus 460 continues operation without interruption. The disclosed method may also comprise engaging the power module 463 with the secondary power supply 462 such that an uninterrupted supply of power is provided to the breathing apparatus.

Figure 7:
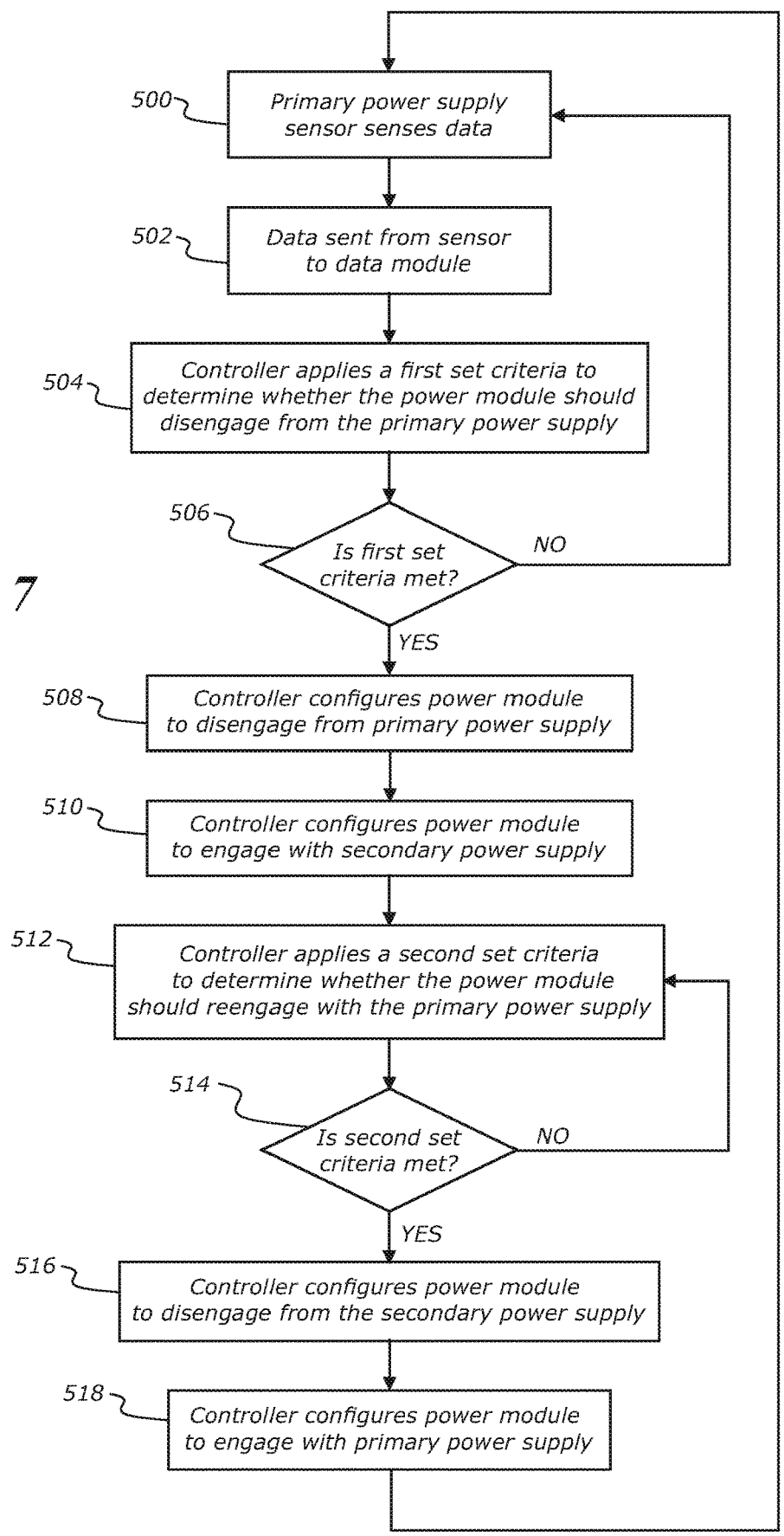
FIG. 7 is a flow diagram illustrating the process of switching power sources between the primary power supply and the secondary power supply.

The preferred methodology of switching between power supplies will now be discussed with reference to FIGS. 6 and 7.

The primary power supply 450 preferably includes a sensor 451 that is configured to measure sensor data indicative of the operating condition of the primary power supply 450 at step 500. Preferably the sensor 451 is configured to transmit the sensor data to the data module 464 of the breathing apparatus 460 at step 502. At steps 504 and 506 the controller 461 applies a first set criteria to determine whether the power module 463 should disengage from the primary power supply 450. More detail on the first set criteria will be provided later. If the first set criteria is not met, the controller 461 takes no further action, and the sensor 451 in the primary power supply 450 continues the collect sensor data at step 500. If the first set criteria is met, the controller 461 proceeds to configure power module 463 to disengage from the primary power supply 450 at step 508, and the controller 461 further configures the power module 463 to engage with the secondary power supply 462 at step 510. The controller 461 configures the power module 463 to provide power from the secondary power supply 462 to the primary power supply 450 following engagement of the secondary power supply 462. Preferably, the sensor 451 is powered by the secondary power supply 462 after engagement of the power module 463 with the secondary power supply 462 via the connection 470. Optionally, the breathing apparatus 460 may sound an alarm at either step 508 or step 510 to alert the patient using the breathing apparatus 460. At step 512, the controller 461 applies a second set criteria to determine whether the power module 463 should reengage with the primary power supply 450. More detail on the second set criteria will be provided later. If the second set criteria is not met, no additional action is taken, and the controller continues to apply the second set criteria at step 512. If the second set criteria is met, the controller 461 configures power module 463 to disengage from the secondary power supply 462 at step 516, and the controller further configures the power module 463 to engage with the primary power supply 450 at step 518. At this point, the primary power supply 450 is now the power source that provides the breathing apparatus 460 with power. The method returns to step 500 again, where the sensor 451 in the primary power supply 450 recommences collecting sensor data that indicative of the operating condition of the primary power supply 450.

In an alternative configuration, the sensor 451 can be disposed within or on the breathing apparatus 460.

2.4.1. First Set Criteria

As explained in steps 504 and 506, the first set criteria is criteria that the controller 461 applies when the primary power supply 450 is powering the breathing apparatus 460. The first set criteria is used to determine whether the breathing apparatus 460 should instead receive power from the secondary power supply 460. The first set criteria is a comparison of the sensor data against a parameter threshold. If the sensor data crosses the parameter threshold for a predetermined length of time, the first set criteria is met, and the controller 461 configures the power module 463 to switch power sources.

The first criteria will now be discussed by way of example with references to FIGS. 7 to 10.

Figure 8:
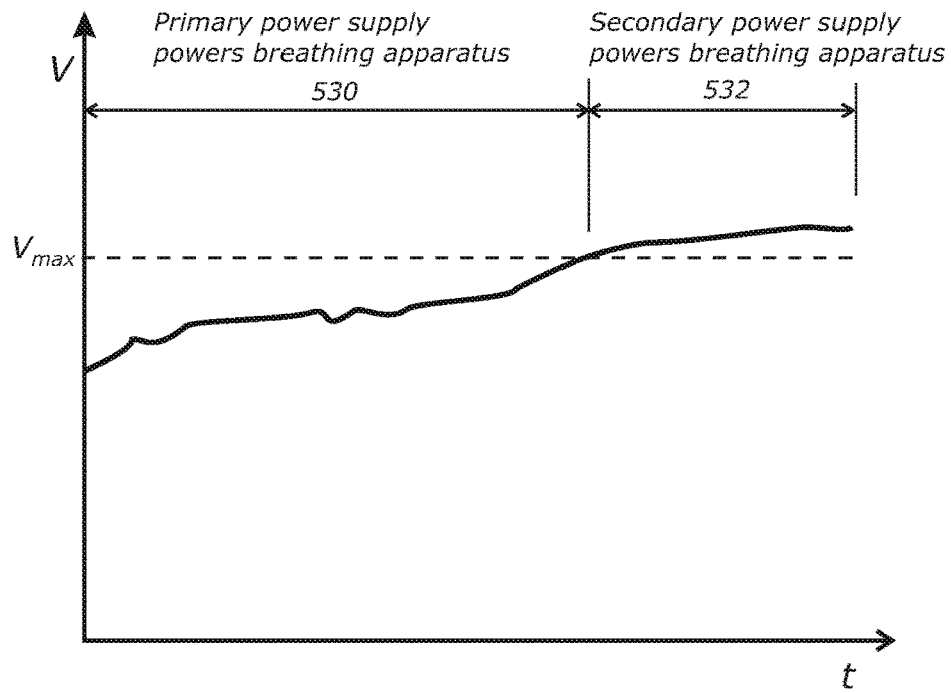
FIG. 8 is a first line graph tracking monitored voltage across time.

FIG. 8 shows an exemplary line graph of the voltage data tracked across time. In this example the primary power supply sensor 451 is collecting voltage data at step 500. The voltage data is transmitted to the data module 463 at step 502. The controller 461 compares the voltage data against a maximum voltage threshold $V_{max}$ at step 504. The first set criteria at step 506 is met when the measured voltage exceeds (or in at least one configuration, is equal to) the maximum voltage threshold $V_{max}$. It is at this point the controller 461 configures the power module 463 to switch power sources at steps 508 and 510. Item 530 represents the time period when the breathing apparatus 460 is powered by the primary power supply 450, and item 532 represents the time period when the breathing apparatus 460 is powered by the secondary power supply 462.

The maximum voltage threshold $V_{max}$ can be seen as an over voltage threshold and/or an over voltage condition of the primary power supply 450. This threshold can be set at a value greater than or equal to the rated voltage. For example this threshold can be set at 100% of the rated voltage. Alternatively it can be 105% of the rated voltage. Alternatively it can be 110% of the rated voltage. Alternatively it can be 115% of the rated voltage. Alternatively it can be 120% of the rated voltage. Alternatively it can be 125% of the rated voltage. Alternatively it can be 130% of the rated voltage. Alternatively it can be 135% of the rated voltage. Alternatively it can be 140% of the rated voltage. Alternatively it can be 145% of the rated voltage. Alternatively it can be 150% of the rated voltage. Alternatively it can be 155% of the rated voltage. Alternatively it can be 160% of the rated voltage.

Figure 9:
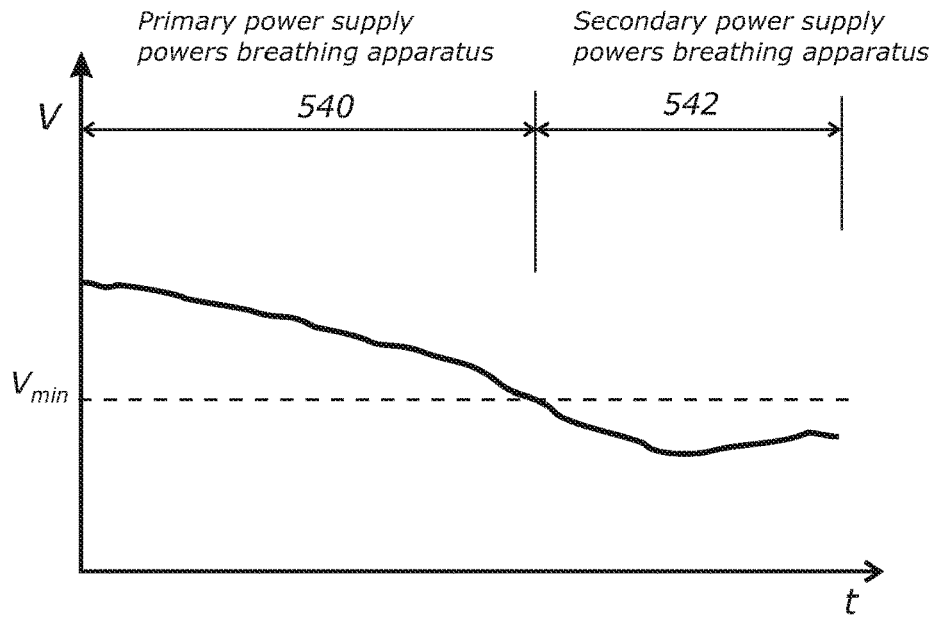
FIG. 9 is a second line graph tracking monitored voltage across time.

FIG. 9 shows another exemplary line graph of the voltage data tracked across time. In this example the primary power supply sensor 451 is collecting voltage data at step 500. The voltage data is transmitted to the data module 463 at step 502. The controller compares the voltage data against a minimum voltage threshold $V_{min}$ at step 504. The first set criteria at step 506 is met when the measured voltage decreases below (or in at least one configuration, is equal to) the minimum voltage threshold $V_{min}$. It is at this point the controller 461 configures the power module 463 to switch power sources at steps 508 and 510. Item 540 represents the time period when the breathing apparatus 460 is powered by the primary power supply 450, and item 542 represents the time period when the breathing apparatus 460 is powered by the secondary power supply 462.

The minimum voltage threshold $V_{min}$ can be seen as an under voltage threshold and/or an under voltage condition of the primary power supply 450. This threshold can be set at a value less than or equal to the rated voltage. For example this threshold can be set at 100% of the rated voltage. Alternatively it can be 95% of the rated voltage. Alternatively it can be 90% of the rated voltage. Alternatively it can be 85% of the rated voltage. Alternatively it can be 80% of the rated voltage. Alternatively it can be 75% of the rated voltage. Alternatively it can be 70% of the rated voltage. Alternatively it can be 65% of the rated voltage. Alternatively it can be 60% of the rated voltage. Alternatively it can be 55% of the rated voltage. Alternatively it can be 50% of the rated voltage. Alternatively it can be 45% of the rated voltage. Alternatively it can be 40% of the rated voltage.

Figure 10:
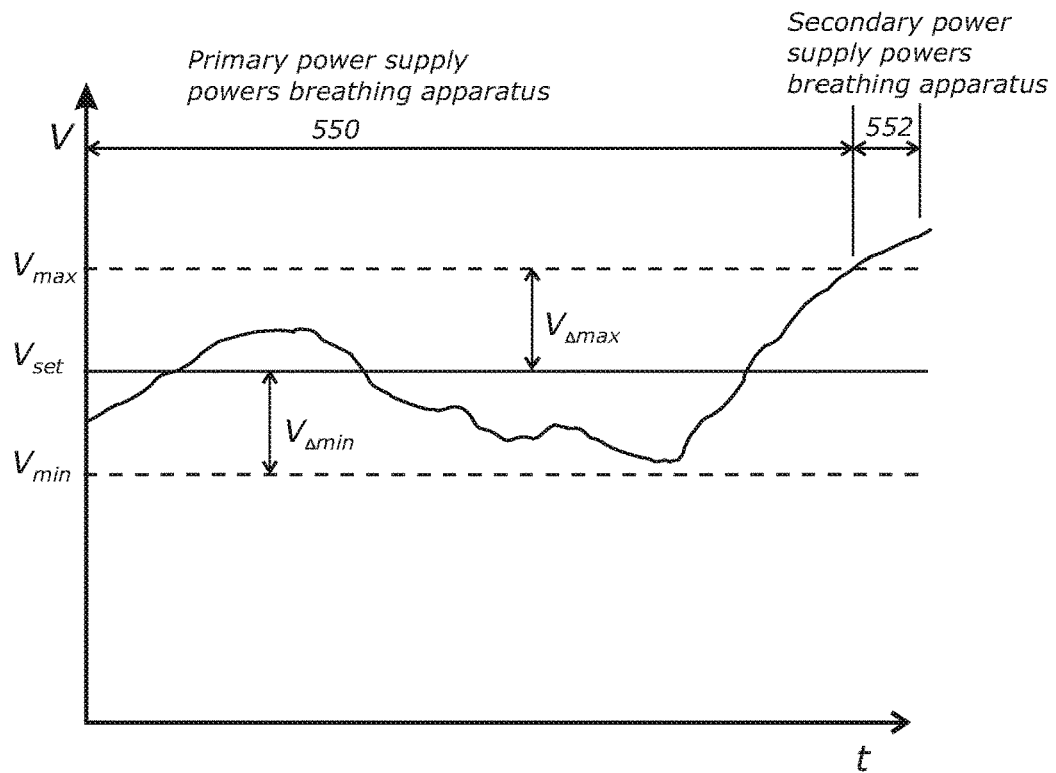
FIG. 10 is a third line graph tracking monitored voltage across time.

FIG. 10 shows another exemplary line graph of the voltage data tracked across time. In this example the primary power supply sensor 451 is collecting voltage data at step 500. The voltage data is transmitted to the data module 463 at step 502. The controller compares the voltage data against a preset voltage $V_{set}$ at step 504. The first set criteria at step 506 is met when the measured voltage deviates too much from the preset voltage $V_{set}$, which happens when the measured voltage either exceeds (or is equal to) the maximum voltage threshold $V_{max}$, or when the measured voltage decreases below (or is equal to) the minimum voltage threshold $V_{min}$. It is at this point the controller 461 configures the power module 463 to switch power sources at steps 508 and 510. Item 550 represents the time period when the breathing apparatus 460 is powered by the primary power supply 450, and item 552 represents the time period when the breathing apparatus is powered by the secondary power supply 462. The maximum voltage threshold $V_{max}$ can be determined based on a predetermined limit $V_{\Delta max}$ that determines the extent the measured voltage is allowed to deviate from the preset voltage $V_{set}$. Likewise, the minimum voltage threshold $V_{min}$ can be determined based on a predetermined limit $V_{\Delta min}$ that determines the extent the measured voltage is allowed to deviate from the preset voltage $V_{set}$. The predetermined limits $V_{\Delta max}$ and $V_{\Delta min}$ can be set to the same deviation from the preset voltage $V_{set}$, or can be set independently. Therefore, the controller 461 can be configured to detect a magnitude of a difference between the parameter threshold and the monitored parameter. If the magnitude of the difference between the parameter threshold and the monitored parameter is zero, or exceeds a value indicative of an equipment fault, the controller 461 configures the power module 463 to switch power sources.

As demonstrated in FIGS. 8 to 10, sensor 451 can be a voltage sensor, and the sensor data is voltage data indicative of an (input) voltage of the primary power supply 450. In this situation, the parameter threshold is indicative of an (input) voltage threshold. The (input) voltage threshold may be indicative of an over voltage threshold of the primary power supply 450 and/or indicative of an over voltage condition, see FIG. 8 for example. Alternatively, the (input) threshold may be indicative of an under voltage threshold of the primary power supply 450 and/or indicative of an under voltage condition, see FIG. 9 for example. Alternatively, as shown in FIG. 10, the (input) thresholds may be indicative of both an over voltage threshold and an under voltage threshold of the primary power supply 450. Alternatively, the (input) thresholds may be indicative of both an over voltage condition and an under voltage condition.

Alternatively the sensor data transmitted by the sensor 451 is power data indicative of the supply of power from the primary power supply 450 to the breathing apparatus 460. In this situation, the parameter threshold is indicative of an (input) power threshold. The (input) power threshold may be indicative of an over power threshold of the primary power supply 450 and/or indicative of an over power condition. Alternatively, the (input) threshold may be indicative of an under power threshold of the primary power supply 450 and/or indicative of an under power condition of the primary power supply 450.

Alternatively the sensor 451 is a temperature sensor, and the sensor data is temperature data indicative of a temperature of the primary power supply 450. In this situation, the parameter threshold is indicative of an (input) temperature threshold. The (input) temperature threshold may be indicative of an over temperature threshold of the primary power supply 450 and/or indicative of an over temperature condition of the primary power supply 450. Alternatively, the (input) threshold may be indicative of an under temperature threshold of the primary power supply 450 and/or indicative of an under temperature condition of the primary power supply 450.

The maximum temperature threshold $T_{max}$ can be seen as an over temperature threshold and/or an over temperature condition of the primary power supply 450. This threshold can be set at a value greater than or equal to the rated temperature. The rated temperature may be a predetermined temperature setting, the rated operational temperature, or the like. For example this threshold can be set at 100% of the rated temperature. Alternatively it can be 105% of the rated temperature. Alternatively it can be 110% of the rated temperature. Alternatively it can be 115% of the rated temperature. Alternatively it can be 120% of the rated temperature. Alternatively it can be 125% of the rated temperature. Alternatively it can be 130% of the rated temperature. Alternatively it can be 135% of the rated temperature. Alternatively it can be 140% of the rated temperature. Alternatively it can be 145% of the rated temperature. Alternatively it can be 150% of the rated temperature. Alternatively it can be 155% of the rated temperature. Alternatively it can be 160% of the rated temperature.

The minimum temperature threshold $T_{min}$ can be seen as an under temperature threshold and/or an under temperature condition of the primary power supply 450. This threshold can be set at a value less than or equal to the rated temperature. The rated temperature may be a predetermined temperature setting, the rated operational temperature, or the like. For example this threshold can be set at 100% of the rated temperature. Alternatively it can be 95% of the rated temperature. Alternatively it can be 90% of the rated temperature. Alternatively it can be 85% of the rated temperature. Alternatively it can be 80% of the rated temperature. Alternatively it can be 75% of the rated temperature. Alternatively it can be 70% of the rated temperature. Alternatively it can be 65% of the rated temperature. Alternatively it can be 60% of the rated temperature. Alternatively it can be 55% of the rated temperature. Alternatively it can be 50% of the rated temperature. Alternatively it can be 45% of the rated temperature. Alternatively it can be 40% of the rated temperature.

It is envisaged that the sensor 451 in the primary power supply 450 can collect and transmit sensor data covering a range of other parameters in addition to voltage, power and temperature as described hereinbefore.

The first set criteria may be met when the measured voltage, power, temperature (or some other parameter) exceeds its maximum threshold for a predetermined period of time. The predetermined period of time can be any length of time, including one or more of: less than 30 seconds (such as for example: 0.01 ms, 0.05 ms, 0.1 ms, 0.5 ms, 1 ms, 2 ms, 5 ms, 10 ms, 20 ms, 500 ms, 1 s, 2 s, 5 s), 30 seconds, 1 minute, 2 minutes, 5 minutes, 10 minutes, 20 minutes, 30 minutes, or 60 minutes, or greater than 60 minutes. Preferably, if the monitored parameter being measured is voltage or power, the predetermined period of time can be one or more of: 0.01 ms, 0.05 ms, 0.1 ms, 0.5 ms, 1 ms, 2 ms, 5 ms, 10 ms, 20 ms, 500 ms, 1 s, 2 s, 5 s. Preferably, if the monitored parameter being measured is temperature, the predetermined period of time can be one or more of: less than 30 seconds, 30 seconds, 1 minute, 2 minutes, 5 minutes, 10 minutes, 20 minutes, 30 minutes, or 60 minutes, or greater than 60 minutes. The (predetermined) period of time can also be a function of the magnitude of a difference between the monitored threshold and the monitored parameter.

The first set criteria may be met when the measured voltage, power, temperature (or some other parameter) decreases below its minimum threshold for a predetermined period of time. The predetermined period of time can be any length of time, including one or more of: less than 30 seconds (such as for example: 0.01 ms, 0.05 ms, 0.1 ms, 0.5 ms, 1 ms, 2 ms, 5 ms, 10 ms, 20 ms, 500 ms, 1 s, 2 s, 5 s), 30 seconds, 1 minute, 2 minutes, 5 minutes, 10 minutes, 20 minutes, 30 minutes, or 60 minutes, or greater than 60 minutes. Preferably, if the monitored parameter being measured is voltage or power, the predetermined period of time can be one or more of: 0.01 ms, 0.05 ms, 0.1 ms, 0.5 ms, 1 ms, 2 ms, 5 ms, 10 ms, 20 ms, 500 ms, 1 s, 2 s, 5 s. Preferably, if the monitored parameter being measured is temperature, the predetermined period of time can be one or more of: less than 30 seconds, 30 seconds, 1 minute, 2 minutes, 5 minutes, 10 minutes, 20 minutes, 30 minutes, or 60 minutes, or greater than 60 minutes. The (predetermined) period of time can also be a function of the magnitude of a difference between the monitored threshold and the monitored parameter.

The first set criteria may be met when the measured voltage, power, temperature (or some other parameter) sufficiently deviates from its preset value for a predetermined period of time. The predetermined period of time can be any length of time, including one or more of: less than 30 seconds (such as for example: 0.01 ms, 0.05 ms, 0.1 ms, 0.5 ms, 1 ms, 2 ms, 5 ms, 10 ms, 20 ms, 500 ms, 1 s, 2 s, 5 s), 30 seconds, 1 minute, 2 minutes, 5 minutes, 10 minutes, 20 minutes, 30 minutes, or 60 minutes, or greater than 60 minutes. Preferably, if the monitored parameter being measured is voltage or power, the predetermined period of time can be one or more of: 0.01 ms, 0.05 ms, 0.1 ms, 0.5 ms, 1 ms, 2 ms, 5 ms, 10 ms, 20 ms, 500 ms, 1 s, 2 s, 5 s. Preferably, if the monitored parameter being measured is temperature, the predetermined period of time can be one or more of: less than 30 seconds, 30 seconds, 1 minute, 2 minutes, 5 minutes, 10 minutes, 20 minutes, 30 minutes, or 60 minutes, or greater than 60 minutes. The (predetermined) period of time can also be a function of the magnitude of a difference between the monitored threshold and the monitored parameter.

2.4.2 Second Set Criteria

As explained in steps 512 and 514, the second set criteria is criteria that the controller 461 applies when the secondary power supply 462 is powering the breathing apparatus 460. The second set criteria is used to determine whether the breathing apparatus 460 should instead receive power from the primary power supply 450.

Preferably, the second set criteria may be met at step 514 when the power module 463 has engaged with the secondary power supply 462 for a (fixed) period of time. After a period of time (step 514), the controller 461 is configured to disengage the power module 463 from the secondary (internal) power supply 462 (step 516), and engage the power module 463 with the primary power supply 450 (step 518). Preferably, the period of time is a predetermined period of time. The predetermined period of time can be any length of time, including one or more of: less than 30 seconds, 30 seconds, 1 minute, 2 minutes, 5 minutes, 10 minutes, 20 minutes, 30 minutes, or 60 minutes, or greater.

Alternatively, the second set criteria may be met as soon as the first set criteria, as described hereinbefore is no longer satisfied. At which point, the breathing apparatus 460 reverts back to the primary power supply 450 as a source of power. In this situation, the sensor 451 in the primary power supply 450 is powered by the secondary power supply 460, and continues to collect sensor data (this may be voltage, power, temperature, or the like). The controller 461 receives the transmitted data to apply the second set criteria.

Using FIG. 8 as an example, the second set criteria may be met as soon as the measured voltage increases above the maximum voltage threshold $V_{max}$, or increases above the voltage threshold $V_{max}$ after a period of time described hereinbefore.

Using FIG. 9 as an example, the second set criteria may be met as soon as the measured voltage decreases below the minimum voltage threshold $V_{min}$, or decreases below the voltage threshold $V_{min}$ after a period of time described hereinbefore.

Using FIG. 10 as an example, the second set criteria may be met as soon as the measured voltage returns to a value falling proximal to the preset voltage $V_{set}$ and/or returns to a value falling in a range between the minimum voltage threshold $V_{min}$ and the maximum voltage threshold $V_{max}$. Likewise, the second set criteria may be met when the measured voltage returns to a value falling proximal to the preset voltage $V_{set}$ after a period of time described hereinbefore; and/or returns to a value falling in a range between the minimum voltage threshold $V_{min}$ and the maximum voltage threshold $V_{max}$ after a period of time described hereinbefore.

In addition to voltage, it is envisaged that the monitored parameter for applying the second set criteria may instead be another parameter, such as power, temperature, or the like.

In at least one configuration, there can be a delay between the detection that the first set criteria, as described hereinbefore is no longer satisfied. The delay can be a fixed delay, for example 2 seconds, or the delay can be a moving delay. The moving delay can be a function of the time during which the first criteria was met. For example, the moving delay can be a duration of approximately 10% of the duration during which the first criteria was met. Alternatively, the moving delay can be a duration of approximately 20%, 30%, 40%, 50%, 60%, 70%, 80%, 90% or 100% of the duration during which the first criteria was met. An advantage of a moving delay is that the breathing apparatus 460 can be protected from instantaneous or short-term changes in state of the condition, for example a rapidly fluctuating supply voltage or power which may damage the device.

3. Peripheral Computing Device Embodiment

Figure 11:
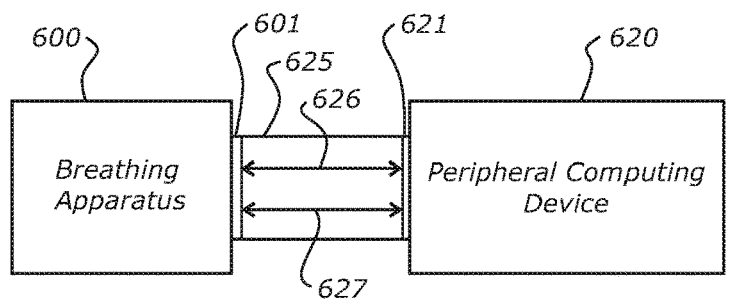
FIG. 11 shows a block diagram of a breathing apparatus connected to a peripheral computing device.
Figure 11:
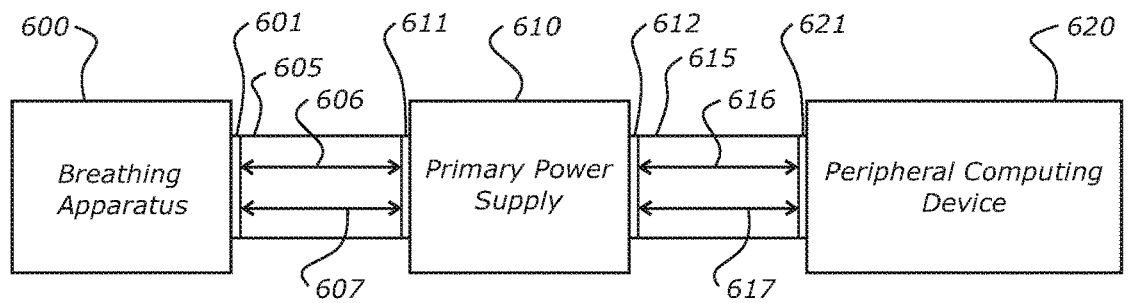

In an alternative embodiment, with reference to FIG. 11, the respiratory therapy system 400 can comprise a breathing apparatus 600 and a peripheral computing device 620 connected to each other 625. The breathing apparatus 600 can be the same as the breathing apparatus 460 as described hereinbefore, although this is not essential and can include variations of the breathing apparatus 460. For example, the breathing apparatus 600 can comprise a secondary power supply 462. In another example, the breathing apparatus 600 can comprise a controller 461. The peripheral computing device 620 can be used to update software on the breathing apparatus 600, or receive (and optionally review) data from the breathing apparatus 600. The peripheral computing device 620 can be a Personal Computer. However the peripheral computing device 620 may also be, but not limited to, a laptop, a smartphone, a tablet, a flash drive, a personal digital assistant, a smartwatch, or the like.

The connector 625 is configured to facilitate transmission of power 626 and data 627 between the breathing apparatus 600 and the peripheral computing device 620. More specifically, the connector 625 is configured to facilitate transmission of power from the peripheral computing device 620 to the breathing apparatus 600, and to facilitate transmission of power from the breathing apparatus 600 to the peripheral computing device 620, thereby providing bi-directional power transfer. Each channel of the bi-directional power transfer facilitated by the connector 625 is independently controllable. The peripheral computing device 620 can supply power to the breathing apparatus 600 via the connector 625 (for example to charge the secondary power supply 462), the breathing apparatus 600 can supply power to the peripheral computing device 620 via the connector 625 (for example to power the peripheral computing device 620 if said device doesn't include its own dedicated power supply, or to charge a battery of the peripheral computing device 620), or both of the aforementioned power supply conditions can be satisfied simultaneously via the connector 625. In at least one configuration, the bi-directional power transfer facilitated by the connector 625 is controlled by a controller 461 of the breathing apparatus 600.

The connector 625 is also configured to facilitate transmission of data from the peripheral computing device 620 to the breathing apparatus 600, and to facilitate transmission of data from the breathing apparatus 600 to the peripheral computing device 620, thereby providing bi-directional data transfer. Each channel of the bi-directional data transfer facilitated by the connector 625 is independently controllable. The peripheral computing device 620 can transfer data to the breathing apparatus 600 via the connector 625, the breathing apparatus 600 can transfer data to the peripheral computing device 620, or both of the aforementioned data transfer conditions can be satisfied simultaneously. In at least one configuration, the bi-directional data transfer facilitated by the connector 625 is controlled by the controller 461 of the breathing apparatus.

In some situations, the primary power supply 610 may be an intermediary to the breathing apparatus 600 and the peripheral computing device 620, where a first intermediary connection 605 (with power connection 606 and data connection 607) connects the breathing apparatus 600 to the primary power supply 610, and a second intermediary connection 615 (with power connection 606 and data connection 607) connects the primary power supply 610 to the peripheral computing device 620. In some embodiments, the peripheral computing device 620 may also act as a substitute to a primary power supply 610 in order to provide an external power source for the breathing apparatus 620. The primary power supply 610 may be the same as the primary power supply 450 as described hereinbefore, although this is not essential and can include variations of the primary power supply 450.

Preferably, the data connection 607, 617, 627 facilitates communication of device data (may also referred to as breathing apparatus data) that is communicated from the breathing apparatus 600 to the peripheral computing device 620. Preferably the device data comprises usage data of the breathing apparatus 600, preferably including but not limited to, pressure, flow, temperature, humidity, compliance, duration, altitude, leak, equipment identification, software, diagnostic and/or user feedback data. Preferably the device data is encrypted. It is envisaged that the device data as described can also be communicated from the peripheral computing device 620 to the breathing apparatus 600.

Preferably, the data connection 607, 617, 627 facilitates communication of peripheral device data that is communicated from the peripheral computing device 620 to the breathing apparatus 600. Preferably the peripheral device data comprises update data. Preferably, the update data comprises updated respiratory therapy settings. The update data also preferably comprises updated operating software and/or firmware. Preferably the peripheral device data comprises a patient profile. The patient profile can comprise patient-specific parameters relevant to said patient's therapy, for example the patient's therapy pressure, humidity settings or other parameters. It is envisaged that the peripheral device data as described can also be communicated from the breathing apparatus 600 to the peripheral computing device 620.

Preferably, the peripheral computing device 620 comprises a peripheral computing device connection 621 that is preferably a peripheral computing device port. The connection 625 between the breathing apparatus 600 and the peripheral computing device 620 can be configured to connect to the peripheral computing device connection 621. Preferably, the peripheral computing device connection 621 comprises a USB port, and more preferably a USB-C port, and even more preferably, the peripheral computing device connection 621 is a female USB-C port (may also be referred to as a female USB-C connector). The connection 625 between the breathing apparatus 600 and the peripheral computing device 620 can be a USB-C connection via a USB-C cable.

In at least one configuration, connections 605, 615, 625 can be the same as connection 470, although this is not essential and can include variations of the connection 470. Connectors 605, 615, 625 may be interchangeable between devices 600, 610 and 620.

In at least one configuration, power connections 606, 616, 626 can be the same as connection 471, although this is not essential and can include variations of the connection 471.

In at least one configuration, data connections 607, 617, 627 can be the same as connection 472, although this is not essential and can include variations of the connection 472.

In at least one configuration, the breathing apparatus 600 comprises a breathing apparatus connection 601 for receiving connection 625. The breathing apparatus connection 601 can be the same as the breathing apparatus connection 473 as described hereinbefore, although this is not essential and can include variations of the breathing apparatus connection 473.

In at least one configuration, the primary power supply 610 comprises primary power supply connections 611 and 612 for receiving connections 605 and 615 respectively. Primary power supply connections 611 and 612 can be the same as primary power supply connection 474 as described hereinbefore, although this is not essential and can include variations of the primary power supply connection 474.

Disclosure is intended to be non-limiting descriptions and multiple variations and embodiments commonly used in the art may be used for implementing this invention.

Preferred embodiments of the invention have been described by way of example only and modifications may be made thereto without departing from the scope of the invention.

The invention claimed is:

1. A respiratory therapy system comprising:
   a primary power supply comprising an external battery pack;
   a breathing apparatus configured to provide respiratory therapy, the apparatus comprising a blower, a humidifier, a controller, and a secondary power supply comprising an internal battery; and
   a USB-C connection between the primary power supply and the breathing apparatus, the connection configured to facilitate transmission of power and data between the primary power supply and the breathing apparatus;

wherein the controller is configured to receive a signal, via a communication link in the USB-C connection, to switch off power to the humidifier in response to the primary power supply running low on reserves, and wherein the respiratory therapy system is configured such that the primary power supply charges the internal battery when the internal battery is not charged to full capacity and the primary power supply is engaged.

2. A respiratory therapy system according to claim 1, wherein the breathing apparatus includes a data module configured to transmit to and receive data from the primary power supply via the connection.

3. A respiratory therapy system according to claim 2, wherein the primary power supply includes a sensor, the primary power supply being configured to transmit sensor data from the sensor to the data module.

4. A respiratory therapy system according to claim 3, wherein the sensor is a temperature sensor and the sensor data is temperature data indicative of a temperature of the primary power supply, and wherein the controller is further configured to monitor a temperature parameter of the primary power supply and disengage the primary power supply in response to the temperature parameter differing from a temperature threshold, wherein the temperature threshold is indicative of an over-temperature condition of the primary power supply.

5. A respiratory therapy system according to claim 3, wherein the sensor is a voltage sensor and the sensor data is voltage data indicative of an input voltage of the primary power supply, and wherein the controller is further configured to monitor an input voltage parameter of the primary power supply and disengage the primary power supply in response to the input voltage parameter differing from an input voltage threshold, the input voltage threshold being indicative of an overvoltage threshold or an undervoltage threshold of the primary power supply.

6. A respiratory therapy system according to claim 3, wherein the sensor data is power data indicative of the supply of power from the primary power supply to the breathing apparatus, and wherein the controller is further configured to monitor an input voltage parameter of the primary power supply and disengage the primary power supply in response to the input voltage parameter differing from an input voltage threshold, the input voltage threshold being indicative of an overvoltage condition or an undervoltage condition.

7. A respiratory therapy system as claimed in claim 1, wherein the connection facilitates simultaneous bi-directional power and data transfer.

8. A respiratory therapy system as claimed in claim 1, wherein the controller is further configured to monitor a parameter of the primary power supply, and disengage the primary power supply in response to the parameter differing from a parameter threshold.

9. A respiratory therapy system as claimed in claim 8, wherein the controller is further configured to engage the secondary power supply on disconnection of the primary power supply such that the breathing apparatus can continue operation without interruption.

10. A respiratory therapy system as claimed in claim 8, wherein the breathing apparatus is configured to be powered by the primary power supply unless the parameter differs from the parameter threshold.

11. A respiratory therapy system as claimed in claim 1, wherein the blower, the humidifier, and the controller operate at a voltage of 12V.

12. A respiratory therapy system as claimed in claim 11, wherein the external battery pack and the internal battery is each at 12V.

13. A respiratory therapy system as claimed in claim 1, wherein the controller is further configured to output an alarm in response to switching to the secondary power supply.

14. A respiratory therapy system as claimed in claim 1, wherein the external battery pack is removable from the breathing apparatus.

15. A respiratory therapy system according to claim 9, wherein the breathing apparatus comprises a power module for controlling power distribution, wherein the controller is configured to monitor the parameter of the primary power supply, and disengage the power module from the primary power supply in response to the parameter differing from the parameter threshold, and wherein the controller is configured to engage the power module with the secondary power supply on disconnection of the primary power supply such that an uninterrupted supply of power is provided to the breathing apparatus.

16. A respiratory therapy system according to claim 15, wherein the controller configures the power module to provide power from the secondary power supply to the primary power supply following engagement of the secondary power supply.

17. A respiratory therapy system according to claim 15, wherein after a period of time, the controller is further configured to disengage the power module from the secondary power supply, and engage the power module with the primary power supply.

18. A respiratory therapy system according to claim 17, wherein the controller is further configured to detect a magnitude of a difference between the parameter threshold and the monitored parameter, the period of time being a function of the difference.

19. A respiratory therapy system according to claim 15, wherein the breathing apparatus includes a circuit that includes the controller, the power module and a data module.

* * * * *